US009155776B2

(12) United States Patent
Klinger

(10) Patent No.: US 9,155,776 B2
(45) Date of Patent: *Oct. 13, 2015

(54) LOW FREQUENCY GLATIRAMER ACETATE THERAPY

(71) Applicant: Yeda Research & Development Co., Ltd., Rehovot (IL)

(72) Inventor: Ety Klinger, Tel Aviv (IL)

(73) Assignee: Yeda Research & Development Co., Ltd., Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/720,556

(22) Filed: May 22, 2015

(65) Prior Publication Data

US 2015/0250845 A1    Sep. 10, 2015

Related U.S. Application Data

(63) Continuation of application No. 14/630,326, filed on Feb. 24, 2015, which is a continuation of application No. 13/770,677, filed on Feb. 19, 2013, now Pat. No. 8,969,302, which is a continuation of application No. 12/806,684, filed on Aug. 19, 2010, now Pat. No. 8,399,413.

(60) Provisional application No. 61/274,687, filed on Aug. 20, 2009, provisional application No. 61/337,612, filed on Feb. 11, 2010.

(51) Int. Cl.
*A61K 38/02* (2006.01)
*A61K 38/07* (2006.01)
*A61K 9/00* (2006.01)

(52) U.S. Cl.
CPC ............... *A61K 38/02* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 3,849,550 A | 11/1974 | Teitelbaum et al. | |
| 4,822,340 A | 4/1989 | Kamstra | |
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,448,225 B2 | 9/2002 | O'Connor et al. | |
| 6,454,746 B1 | 9/2002 | Bydlon et al. | |
| 6,514,938 B1 | 2/2003 | Gad et al. | |
| 6,620,847 B2 | 9/2003 | Konfino et al. | |
| 6,800,285 B2 | 10/2004 | Rodriguez et al. | |
| 6,800,287 B2 | 10/2004 | Gad et al. | |
| 6,844,314 B2 | 1/2005 | Eisenbach-Schwartz et al. | |
| 6,939,539 B2 | 9/2005 | Konfino et al. | |
| 7,022,663 B2 | 4/2006 | Gilbert et al. | |
| 7,033,582 B2 | 4/2006 | Yong et al. | |
| 7,074,580 B2 | 7/2006 | Gad et al. | |
| 7,163,802 B2 | 1/2007 | Gad et al. | |
| 7,199,098 B2 | 4/2007 | Konfino et al. | |
| 7,279,172 B2 | 10/2007 | Aharoni et al. | |
| 7,425,332 B2 | 9/2008 | Aharoni et al. | |
| 7,429,374 B2 | 9/2008 | Klinger | |
| 7,495,072 B2 | 2/2009 | Dolitzky | |
| 7,560,100 B2 | 7/2009 | Pinchasi et al. | |
| 7,615,359 B2 | 11/2009 | Gad et al. | |
| 7,625,861 B2 | 12/2009 | Konfino et al. | |
| 7,855,176 B1 | 12/2010 | Altman et al. | |
| 7,923,215 B2 | 4/2011 | Klinger | |
| 7,928,131 B2 | 4/2011 | Buzard | |
| 7,968,511 B2 | 6/2011 | Vollmer et al. | |
| 8,008,258 B2 | 8/2011 | Aharoni et al. | |
| 8,232,250 B2 * | 7/2012 | Klinger | 514/17.9 |
| 8,367,605 B2 | 2/2013 | Konfino et al. | |
| 8,389,228 B2 | 3/2013 | Klinger | |
| 8,399,211 B2 | 3/2013 | Gad et al. | |
| 8,399,413 B2 * | 3/2013 | Klinger | 514/17.9 |
| 8,709,433 B2 | 4/2014 | Kasper | |
| 8,759,302 B2 | 6/2014 | Dhib-Jalbut | |
| 8,815,511 B2 | 8/2014 | Tchelet et al. | |

(Continued)

FOREIGN PATENT DOCUMENTS

WO    WO 95/31990    11/1995
WO    WO 98/30227    7/1998

(Continued)

OTHER PUBLICATIONS

Dec. 1, 2014 Answer to Counterclaims, filed in connection with *Teva Pharmaceuticals USA, Inc., et al., v. Sandoz Inc. and Momenta Pharmaceuticals, Inc.* in the the United States District Court for District of Delaware (Case No. 1:14-cv-01171-GMS).

Mar. 20, 2015 Answer to Amneal's Counterclaims, filed in connection with *Teva Pharmaceuticals USA, Inc., et al.*, v. *Sandoz Inc. and Amneal Pharmaceuticals LLC*, in the United States District Court for District of Delaware (Case No. 1:14-cv-01171-GMS).

(Continued)

*Primary Examiner* — John Ulm
(74) *Attorney, Agent, or Firm* — Gary J. Gershik; Cooper & Dunham LLP

(57) ABSTRACT

A method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

30 Claims, No Drawings

(56) References Cited

U.S. PATENT DOCUMENTS

| | | |
|---|---|---|
| 8,920,373 B2 | 12/2014 | Altman et al. |
| 8,969,302 B2 * | 3/2015 | Klinger .................. 514/17.9 |
| 2002/0037848 A1 | 3/2002 | Eisenbach-Schwartz et al. |
| 2002/0077278 A1 | 6/2002 | Yong et al. |
| 2004/0106554 A1 | 6/2004 | Konfino et al. |
| 2005/0014694 A1 | 1/2005 | Yong |
| 2005/0019322 A1 | 1/2005 | Rodriguez et al. |
| 2005/0170004 A1 | 8/2005 | Rosenberger et al. |
| 2005/0171286 A1 | 8/2005 | Konfino et al. |
| 2005/0277885 A1 | 12/2005 | Scherer |
| 2006/0154862 A1 | 7/2006 | Ray et al. |
| 2006/0172942 A1 | 8/2006 | Dolitzky |
| 2006/0189527 A1 | 8/2006 | Rasmussen et al. |
| 2006/0194725 A1 | 8/2006 | Rasmussen et al. |
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0037740 A1 | 2/2007 | Pinchasi et al. |
| 2007/0048794 A1 | 3/2007 | Gad et al. |
| 2007/0054857 A1 | 3/2007 | Pinchasi et al. |
| 2007/0059798 A1 | 3/2007 | Gad |
| 2007/0161566 A1 | 7/2007 | Pinchasi |
| 2007/0173442 A1 | 7/2007 | Vollmer |
| 2007/0244056 A1 | 10/2007 | Hayardeny et al. |
| 2008/0118553 A1 | 5/2008 | Frenkel et al. |
| 2008/0207526 A1 | 8/2008 | Strominger |
| 2008/0261894 A1 | 10/2008 | Kreitman et al. |
| 2009/0048181 A1 | 2/2009 | Schipper et al. |
| 2009/0053253 A1 | 2/2009 | Klinger |
| 2009/0149541 A1 | 6/2009 | Stark et al. |
| 2010/0160894 A1 | 6/2010 | Julian et al. |
| 2010/0167983 A1 | 7/2010 | Kreitman et al. |
| 2010/0210817 A1 | 8/2010 | Gad et al. |
| 2010/0285600 A1 | 11/2010 | Lancet et al. |
| 2010/0298227 A1 | 11/2010 | Aharoni et al. |
| 2010/0305023 A1 | 12/2010 | Stark et al. |
| 2011/0046065 A1 | 2/2011 | Klinger |
| 2011/0060279 A1 | 3/2011 | Altman et al. |
| 2011/0066112 A1 | 3/2011 | Altman et al. |
| 2012/0027718 A1 | 2/2012 | Kreitman et al. |
| 2012/0309671 A1 | 12/2012 | Klinger |
| 2014/0107208 A1 | 4/2014 | Comabella et al. |
| 2014/0193827 A1 | 7/2014 | Schwartz et al. |
| 2014/0271532 A1 | 9/2014 | Kreitman et al. |
| 2014/0271630 A1 | 9/2014 | Vollmer |
| 2014/0294899 A1 | 10/2014 | Kasper et al. |
| 2014/0322158 A1 | 10/2014 | Dhib-Jalbut |
| 2015/0045306 A1 | 2/2015 | Tchelet et al. |

FOREIGN PATENT DOCUMENTS

| | | |
|---|---|---|
| WO | WO 00/05250 | 2/2000 |
| WO | WO 00/05249 | 3/2000 |
| WO | WO 00/18794 | 4/2000 |
| WO | WO 00/20010 | 4/2000 |
| WO | WO 00/27417 | 5/2000 |
| WO | WO 01/060392 | 8/2001 |
| WO | WO 01/93828 | 12/2001 |
| WO | WO 01/97846 | 12/2001 |
| WO | WO 03/048735 | 6/2003 |
| WO | WO 2004/103297 | 2/2004 |
| WO | WO 2004/043995 | 5/2004 |
| WO | WO 2004/064717 | 8/2004 |
| WO | WO 2004/091573 | 10/2004 |
| WO | WO 2005/041933 | 5/2005 |
| WO | WO 2005/084377 | 9/2005 |
| WO | WO 2005/120542 | 12/2005 |
| WO | WO 2006/029036 | 3/2006 |
| WO | WO 2006/029393 | 3/2006 |
| WO | WO 2006/029411 | 3/2006 |
| WO | WO 2006/050122 | 5/2006 |
| WO | WO 2006/083608 | 8/2006 |
| WO | WO 2006/089164 | 8/2006 |
| WO | WO 2006/116602 | 11/2006 |
| WO | WO 2007/030573 | 3/2007 |
| WO | WO 2007/081975 | 7/2007 |
| WO | WO 2008/006026 | 1/2008 |
| WO | WO 2009/070298 | 6/2009 |
| WO | WO 2011/008274 | 1/2011 |
| WO | WO 2011/022063 | 2/2011 |
| WO | WO 2012/051106 | 4/2012 |
| WO | WO 2013/055683 | 4/2013 |
| WO | WO 2014/058976 | 4/2014 |
| WO | WO 2014/107533 | 7/2014 |
| WO | WO 2014/165280 | 10/2014 |

OTHER PUBLICATIONS

Dec. 1, 2014 Answer to Counterclaims, filed in connection with *Teva Pharmaceuticals USA, Inc., et al.*, v. *Doctor Reddy's Laboratories Ltd. and Doctor Reddy's Laboratories, Inc.* in the United States District Court for the District of Delaware (Case No. 1:14-cv-01172-GMS).

Nov. 26, 2014 Answer, filed in connection with *Teva Pharmaceuticals USA, Inc., et al.*, v. *Mylan Pharmaceuticals Inc., Mylan Inc. and Natco Pharma Ltd*. In the United States District Court for the Northern District of West Virginia (Case. No. 1:14-cv-00167-IMK).

Jan. 23, 2015 Answer, filed in connection with *Teva Pharmaceuticals USA, Inc., et al.*, v. *Synthon Pharmaceuticals Inc., et al*. In the United States District Court for the District of Delaware (Case. No. 1:14-cv-01419-UNA).

Feb. 17, 2015 Answer to Counterclaims, filed in connection with *Teva Pharmaceuticals USA, Inc., et al.*, v. *Synthon Pharmaceuticals Inc., et al*. In the United States District Court for the District of Delaware (Case. No. 1:14-cv-01419-UNA).

Feb. 12, 2015 Plaintiff's Notice of Voluntary Dismissal, filed in connection with *Teva Pharmaceuticals USA, Inc., et al.*, v. *Synthon Pharmaceuticals Inc., et al.* in the United States District Court for the Middle District of North Carolina (Case. No. 1:14-cv-975).

Feb. 3, 2015 Complaint, filed in connection with *Teva Pharmaceuticals USA, Inc., et al.*, v. *Amneal Pharmaceuticals LLC* in the United States District Court for the District of Delaware (Case. No. 1:15-cv-00124-GMS).

Feb. 24, 2015 Answer, filed in connection with *Teva Pharmaceuticals USA, Inc., et al.*, v. *Amneal Pharmaceuticals LLC* in the United States District Court for the District of Delaware (Case. No. 1:15-cv-00124-GMS).

A Study to Test the Effectiveness and Safety of a New Higher 40mg Dose of Copaxone® Compared to Copaxone® 20mg, the Currently Approved Dose [online]. ClinicalTrials.gov, 1993 [retrieved on Sep. 3, 2014]. Retrieved from the Internet: <URL: clinicaltrials.gov/show/NCT00202982>.

Sep. 10, 2014 Complaint, filed in connection with *Teva Pharmaceuticals USA, Inc., et al.*, v. *Sandoz Inc. and Momenta Pharmaceuticals, Inc.* in the the United States District Court for District of Delaware (Case No. 1:14-cv-01171-GMS).

Nov. 3, 2014 Answer, filed in connection with *Teva Pharmaceuticals USA, Inc., et al.*, v. *Sandoz Inc. and Momenta Pharmaceuticals, Inc.* in the United States District Court for the District of Delaware (Case No. 1:14-cv-01171-GMS.

Sep. 10, 2014 Complaint, filed in connection with *Teva Pharmaceuticals USA, Inc., et al.*, v. *Doctor Reddy's Laboratories Ltd. and Doctor Reddy's Laboratories, Inc.* in the United States District Court for the District of Delaware (Case No. 1:14-cv-01172-GMS).

Nov. 3, 2014 Answer, filed in connection with Teva Pharmaceuticals USA, Inc., et al., v. Doctor Reddy's Laboratories Ltd. and Doctor Reddy's Laboratories, Inc.in the United States District Court for the District of Delaware (Case No. 1:14-cv- 01172-GMS).

Sep. 11, 2014 Complaint, filed in connection with Teva Pharmaceuticals USA, Inc., et al. v. Doctor Reddy's Laboratories Ltd., Doctor Reddy's Laboratories, Inc., Sandoz, Inc., and Momenta Pharmaceuticals in the United States District Court for the District of New Jersey (Case No. 3:14-cv-05672-MAS-TJB.

Nov. 25, 2014 Plaintiff's Notice of Voluntary Dismissal, filed in connection with *Teva Pharmaceuticals USA, Inc., et al.* v. *Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).

(56) References Cited

OTHER PUBLICATIONS

Oct. 6, 2014 Complaint, filed in connection with *Teva Pharmaceuticals USA, Inc., et al.,* v. *Mylan Pharmaceuticals Inc., and Natco Pharma Ltd.* in the United States District Court for the District of Delaware (Case No. 1:14-cv-01278-GMS).

Oct. 7, 2014 Complaint, filed in connection with *Teva Pharmaceuticals USA, Inc., et al.,* v. *Mylan Pharmaceuticals Inc., Mylan Inc. and Natco Pharma Ltd.* In the United States District Court for the Northern District of West Virginia (Case. No. 1:14-cv-00167-IMK).

Nov. 18, 2014 Complaint, filed in connection with *Teva Pharmaceuticals USA, Inc., et al.,* v. *Synthon Pharmaceuticals Inc., et al.* in the United States District Court of Delaware (Case. No. 1:14-cv-01419-UNA).

Nov. 19, 2014 Complaint, filed in connection with *Teva Pharmaceuticals USA, Inc., et al.,* v. *Synthon Pharmaceuticals Inc., et al.* in the United States District Court for the Middle District of North Carolina (Case. No. 1:14-cv-975).

Costello, K., et al., 'Recognizing Nonadherence in Patients with Multiple Sclerosis and Maintaining Treatment Adherence in the Long Term,' Medscape J Med., vol. 10(9):225 (2008).

Edgar, C.M., et al., 'Lipoatrophy in Patients with Multiple Sclerosis on Glatiramer Acetate,' Can. J. Neurol. Sci., vol. 31:58-63 (2004).

Ford, CC., et al. 'A Prospective open-label study of glatiramer acetate: over a decade of continuous use in multiple sclerosis patients,' Multiple Sclerosis, vol. 12:309-320 (2006).

Gagnon, L., "Every-Other-Day Dosing of Glatiramer Acetate Reduces Adverse Reactions With Comparable Efficacy to Daily Dosing: Presented at WCTRMS," PeerView Press, (Sep. 21, 2008).

Ge, Y., et al. "Glatiramer Acetate (Copaxone) Treatment in Relapsing-Remitting Multiple Sclerosis", Neurology, vol. 54:813-817 (Feb. 2000).

Johnson, K.P., et al., 'Copolymer 1 reduces relapse rate and improves disability in relapsing-remitting multiple sclerosis: Results of a phase III multicenter, double-blind, placebo-controlled trial,' Neurology, vol. 45:1268-1276 (Jul. 1995).

Klauer, T., and Zettl, U.K., 'Compliance, adherence, and the treatment of multiple sclerosis,' J Neural. vol. 255 (Suppl. 6):87-92 (2008).

Lisak, R.P. and Kira, J., 'Chapter 100, Multiple Sclerosis,' International Neurology, 366-374 (2009).

Manso, P.J., and Sokol, A.L., "Life cycle management of ageing pharmaceutical assets," Pharmaceutical Law Insight, vol. 3(7):16-19 (Jul./Aug. 2007).

A Study to Test the Effectiveness and Safety of a New Higher 40mg Dose of Copaxone® Compared to Copaxone® 20mg, the Currently Approved Dose [online]. ClinicalTrials.gov, 1993 [retrieved on Feb. 13, 2015]. Retrieved from the Internet: <URL:clinicaltrials.gov/show/NCT00202982>.

Copaxone®, Physicians' Desk Reference, 62nd ed. Montvale, NJ, Thomson Healthcare Inc., pp. 3231-3235 (2008).

Rebif® (interferon beta-1a), Product Description, 103795.5062PI final Jun. 7, 2005.

This Is MS Multiple Sclerosis Community: Knowledge & Support [online]. ThisIsMS [retrieved on Sep. 3, 2014]. Retrieved from the Internet: <URL:www.thisisms.com/forum/copaxonef4/topic5610.html>.

May 26, 2015 Yeda's Patent Owner Preliminary Response filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).

May 26, 2015 Yeda's Patent Owner Preliminary Response filed in connection with *Mylan Pharmaceuticals Inc.* v. *Yeda Research & Development Co. Ltd.* for U.S. Patent No. 8,399,413 in the United States Patent and Trademark Office Patent Trial and Appeal Board (Case No. IPR2015-00644).

Jun. 19, 2015 Yeda's Patent Owner Preliminary Response filed in connection with *Mylan Pharmaceuticals Inc.* v. *Yeda Research & Development Co. Ltd.* For U.S. Patent No. 8,969,302 in the United States Patent and Trademark Office Patent Trial and Appeal Board (Case No. IPR2015-00830).

Teva Provides Update on Forte Trial, published on Jul. 7, 2008 at Jerusalem, Israel by Teva Pharmaceutical Industries Ltd., submitted as Exhibit 2001 in Inter Partes Review Case Nos. IPR2015-00643 and IPR2015-00644 and IPR2015-00830.

Franscisco J. Quintana et al., "Systems Biology Approaches for the Study of Multiple Sclerosis", 12 J. Cell. Mol. Med. 4, 1087-93 (2008); submitted as Exhibit 2002 in Inter Partes Review Case Nos. IPR2015-00643 and IPR2015-00644 and 1PR2015-00830.

David J. Virley, "Developing Therapeutics for the treatment of multiple sclerosis", 2 The Journal of the American Society for Experimental NeuroTherapeutics, 638-49 (Oct. 2005), submitted as Exhibit 2003 in Inter Partes Review Case Nos. IPR2015-00643 and IPR2015-00644 and IPR2015-00830.

Manuel A. Friese et al., "The value of animal models for drug development in multiple sclerosis", 129 Brain, 1940-52 (2006), submitted as Exhibit 2004 in Inter Partes Review Case Nos. IPR2015-00643 and IPR2015-00644 and IPR2015-00830.

Copaxone®, Food and Drug Administration Approved Labeling, Jan. 2014, submitted as Exhibit 2005 in Inter Partes Review Case Nos. IPR2015-00643 and IPR2015-00644 and IPR2015-00830.

Dvora Teitelbaum et al., "Suppression of experimental allergic encephalomyelitis by a synthetic polypeptide", 1 Eur. J. Immunol., 242-248 (Aug. 1971), submitted as Exhibit 2006 in Inter Partes Review Case Nos. IPR2015-00643 and IPR2015-00644 and IPR2015-00830.

Jill Conner, "Glatiramer acetate and therapeutic peptide vaccines for multiple sclerosis", 1 J. Autoimmunity and Cell Responses 3 (2014), submitted as Exhibit 2007 in Inter Partes Review Case Nos. IPR2015-00643 and IPR2015-00644 and IPR2015-00830.

Copaxone®, Physicians' Desk Reference, 62nd ed. Montvale, NJ, . Thomson Healthcare Inc., pp. 3231-3235 (2008), submitted as Exhibit 2008 in Inter Partes Review Case Nos. IPR2015-00643 and IPR2015-00644 and IPR2015-00830.

Wiebke Schrempf and Tjalf Ziemssen, "Glatiramer acetate: Mechanisms of action in multiple sclerosis", 6 Autoimmunity Reviews, 469-475 (2007), submitted as Exhibit 2009 in Inter Partes Review Case Nos. IPR2015-00643 and IPR2015-00644 and IPR2015-00830.

V. Wee Yong, "Differential mechanisms of action of interferon-62 and glatiramer acetate in MS", 59 Neurology, 802-8 (Apr. 2002), submitted as Exhibit 2010 in Inter Partes Review Case Nos. IPR2015-00643 and IPR2015-00644 and IPR2015-00830.

Suhayl Dhib-Jalbut, "Mechanisms of action of interferons and glatiramer acetate in multiple sclerosis", 58 Neurology (8 Suppl 4), S3-9 (2002), submitted as Exhibit 2011 in Inter Partes Review Case Nos. IPR2015-00643 and IPR2015-00644 and IPR2015-00830.

Oliver Neuhaus et al., "Pharmacokinetics and pharmacodynamics of the interferon-betas, glatiramer acetate, and mitoxantrone in multiple sclerosis", 259 Journal of the Neurological Sciences, 27-37 (2007), submitted as Exhibit 2012 in Inter Partes Review Case Nos. IPR2015-00643 and IPR2015-00644 and IPR2015-00830.

Oded Abramsky et al., "Effect of a Synthetic Polypeptide (COP 1) on Patients With Multiple Sclerosis and With Acute Disseminated Encephalomyelitis. Preliminary Report", 31 Journal of the Neurological Sciences, 433-38 (1977), submitted as Exhibit 2013 in Inter Partes Review Case Nos. IPR2015-00643 and IPR2015-00644 and IPR2015-00830.

Murry B. Bornstein et al., "Treatment of Multiple Sclerosis with a Synthetic Polypeptide: Preliminary Results", in *Transactions of the American Neurological Association,* 1980, vol. 105 (New York, Springer Publishing Company), pp. 348-350, submitted as Exhibit 2014 in Inter Partes Review Case Nos. IPR2015-00643 and IPR2015-00644 and IPR2015-00830.

Murry B. Bornstein et al., "Treatment Multiple Sclerosis: Trial of a Synthetic Polypeptide", 11 Ann. Neurol., 317-19 (Mar. 1982), submitted as Exhibit 2015 in Inter Partes Review Case Nos. IPR2015-00643 and IPR2015-00644 and 1PR2015-00830.

Murry B. Bornstein et al., "A Pilot Trial of Cop 1 in Exacerbating-Remitting Multiple Sclerosis", 13 N. Engl. J. Med., 408-14 (Aug. 13,

(56) References Cited

OTHER PUBLICATIONS

1987), submitted as Exhibit 2016 in Inter Partes Review Case Nos. IPR2015-00643 and IPR2015-00644 and IPR2015-00830.

Table of Contents—Sep. 2008; 14(1 suppl) [online]. Sage Journals [retrieved May 22, 2015]. Retrieved from the Internet: <URL msj.sagepub.com/content/14/1_suppl.toc>, submitted as Exhibit 2017 in Inter Partes Review Case Nos. IPR2015-00643 and IPR2015-00644 and IPR2015-00830.

Massimo Filippi et al., "Effects of oral glatiramer acetate on clinical and MRI monitored disease activity in patients with relapsing multiple sclerosis: a multicentre, double-blind, randomised, placebo-controlled study", Lancet Neurol. Jan. 20, 2006 [online], Retrieved from the Internet <URL:neurology.thelancet.com> <DOI:10.1016/S1474-4422(06)70327-1>, submitted as Exhibit 2018 in Inter Partes Review Case Nos. IPR2015-00643 and IPR2015-00644 and IPR2015-00830.

Yuval Ramot et al., "Comparative Long-Term Preclinical Safety Evaluation of Two Glatiramoid Compounds (Glatiramer Acetate, Copaxonel, and TV- 5010, Protiramer) in Rats and Monkeys", 40 Toxicol. Path., 40-54 (2012), submitted as Exhibit 2019 in Inter Partes Review Case Nos. IPR2015-00643 and IPR2015-00644 and IPR2015-00830.

U.S. Appl. No. 2007/0161566 A1 ("Pinchasi"), submitted as Exhibit 2020 in Inter Partes Review Case Nos. IPR2015-00643 and IPR2015-00644 and IPR2015-00830.

Tjalf Ziemssen et al., "Risk-Benefit Assessment of Glatiramer Acetate in Multiple Sclerosis", 24 Drug Safety, 13, 979-90 (2001), submitted as Exhibit 2021 in Inter Partes Review Case Nos. IPR2015-00643 and IPR2015-00644 and IPR2015-00830.

"News Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis" [online] Teva Pharmaceutical Industries Ltd. Jul. 1, 2013 [retrieved on May 22, 2015]. Retrieved from the Internet: <URL://ir.tevapharm.com/phoenix.zbtml?c=73925&p=irol-newsArticle Print&ID=1834170>, submitted as Exhibit 2022 in Inter Partes Review Case Nos. IPR2015-00643 and IPR2015-00644 and IPR2015-00830.

Omar Khan et al., "Three Times Weekly Glatiramer Acetate in Relapsing-Remitting Multiple Sclerosis", 73 Ann. Neurol., 705-13 (2013), submitted as Exhibit 2023 in Inter Partes Review Case Nos. IPR2015-00643 and IPR2015-00644 and IPR2015-00830.

"Teva Reports First Quarter 2015 Results", Apr. 30, 2015, Jerusalem, Teva Press Release, submitted as Exhibit 2024 in Inter Partes Review Case Nos. IPR2015-00643 and IPR2015-00644 and IPR2015-00830.

Kate McKeage, "Glatiramer Acetate 40 mg/mL in Relapsing-Remitting Multiple Sclerosis: A Review", CNS Drugs, Apr. 24, 2015, submitted as Exhibit 2025 in Inter Partes Review Case Nos. IPR2015-00643 and IPR2015-00644 and IPR2015-00830.

K.P. Johnson et al., "Copolymer 1 reduces relapse rate and improves disability in relapsing-remitting multiple sclerosis: Results of a phase I11 multicenter, double-blind, placebo-controlled trial", 45 Neurology, 1268-76 (1995), submitted as Exhibit 2026 in Inter Partes Review Case Nos. IPR2015-00643 and IPR2015-00644 and IPR2015-00830.

*Webster's Ninth New Collegiate Dictionary*, Merriam-Webster, Inc., 1985, p. 872, submitted as Exhibit 2027 in Inter Partes Review Case No. IPR2015-00830.

U.S. Appl. No. 14/630,326, filed Feb. 24, 2015 (Klinger).

U.S. Appl. No. 14/520,280, filed Oct. 21, 2014 (Tchelet et al.).

U.S. Appl. No. 11/228,850, filed Sep. 14, 2005 (Schwartz et al.). The specification and claims as originally filed.

U.S. Appl. No. 11/654,374, filed Jan. 16, 2007 (Schwartz et al.). The specification and claims as originally filed.

U.S. Appl. No. 09/359,099, filed Jul. 22, 1999 (Strominger et al.). The specification and claims as originally filed.

Reissue Application in connection with U.S. Appl. No. 13/964,856, filed Aug. 12, 2013 (Konfino et al.).

Request for Ex Parte Re-examination by Third Party in connection with U.S. Appl. No. 90/013,249, filed May 21, 2014 (Konfino et al.).

Oct. 10, 2012 Office Action, issued in connection With U.S. Appl. No. 12/761,367, filed Apr. 15, 2010.

Jul. 3, 2012 Response, filed in connection With U.S. Appl. No. 12/761,367, filed Apr. 15, 2010.

Jun. 4, 2012 Office Action, issued in connection With U.S. Appl. No. 12/761,367, filed Apr. 15, 2010.

Nov. 1, 2010 Notice of Allowance, issued in connection with U.S. Appl. No. 12/785,125, filed May 21, 2010.

Jun. 10, 2014 Office Action, issued in connection with U.S. Appl. No. 12/948,611, filed Nov. 17, 2010.

Oct. 6, 2014 Response, filed in connection with U.S. Appl. No. 12/948,611, filed Nov. 17, 2010.

Dec. 24, 2014 Notice of Allowance, issued in connection with U.S. Appl. No. 12/948,611, filed Nov. 17, 2010.

Dec. 16, 2013 Office Action, issued in connection with U.S. Appl. No. 13/384,021, filed May 25, 2012.

Mar. 17, 2014 Response, filed in connection with U.S. Appl. No. 13/384,021, filed May 25, 2012.

May 8, 2014 Notice of Allowance, issued in connection with U.S. Appl. No. 13/384,021, filed May 25, 2012.

Sep. 3, 2014 Decision to discontinue the opposition proceedings in connection with European Patent No. EP2275086.

Mar. 25, 2013 Office Action, issued in connection with Taiwanese Patent Application No. 100103482 together with an English language translation thereof.

Sep. 25, 2013 Communication in Response to Mar. 25, 2013 Office Action, filed in connection with Taiwanese Patent Application No. 100103482 together with an English language translation thereof.

Feb. 25, 2014 Office Action, issued in connection with Mexican Patent Application No. MX/a/2012/000687 together with an English language summary thereof.

Jun. 25, 2014 Amendment in Response to Feb. 25, 2014 Office Action, filed in connection with Mexican Patent Application No. MX/a/2012/000687 together with an English language translation thereof.

Oct. 10, 2014 Office Action, issued in connection with Mexican Patent Application No. MX/a/2012/000687 together with an English language summary thereof.

Dec. 19, 2014 Amendment in Response to Oct. 20, 2014 Office Action, filed in connection with Mexican Patent Application No. MX/a/2012/000687 together with an English language translation thereof.

Mar. 4, 2015 Office Action, issued in connection with Mexican Patent Application No. MX/a/2012/000687 together with an English language summary thereof.

Dec. 11, 2014 Amendment in Response to Aug. 11, 2014 Official Action, filed in connection with Eurasian Patent Application No. 201270167 together with an English language translation thereof.

Aug. 11, 2014 Office Action, issued in connection with Eurasian Patent Application No. 201270167 together with an English language translation thereof.

Mar. 21, 2014 Office Action, issued in connection with Eurasian Patent Application No. 201270167 together with an English language translation thereof.

Jul. 21, 2014 Amendment in Response to Mar. 21, 2014 Official Action, filed in connection with Eurasian Patent Application No. 201270167 together with an English language translation thereof.

Feb. 14, 2014 Amendment in Response to Oct. 16, 2013 Office Action, filed in connection with Eurasian Patent Application No. 201270167 together with an English language.

Oct. 16, 2013 Office Action, issued in connection with Eurasian Patent Application No. 201270167 together with an English language translation thereof.

Aug. 19, 2014 Office Action, issued in connection with Japanese Patent Application No. 2012-520598 together with an English language translation thereof.

Dec. 19, 2014 Amendment in Response to Aug. 19, 2014 Office Action, filed in connection with Japanese Patent Application No. 2012-520598 together with an English language translation thereof.

(56) References Cited

OTHER PUBLICATIONS

Jul. 18, 2013 Application to Amend a Complete Specification, filed in connection with South African Application No. 2012/00586 (Klinger).
Jul. 9, 2013 Office Action Issued in Connection With U.S. Appl. No. 13/770,677, filed Feb. 19, 2013 (Klinger).
Amendment in Response to Jul. 9, 2013 Office Action filed Dec. 9, 2013 in Connection With U.S. Appl. No. 13/770,677, filed Feb. 19, 2013 (Klinger).
Feb. 5, 2014 Office Action Issued in Connection With U.S. Appl. No. 13/770,677, filed Feb. 19, 2013 (Klinger).
Amendment in Response to Feb. 5, 2014 Office Action filed Aug. 5, 2014 in Connection With U.S. Appl. No. 13/770,677, filed Feb. 19, 2013 (Klinger).
Notice of Allowance issued Oct. 24, 2014 issued in Connection With U.S. Appl. No. 13/770,677, filed Feb. 19, 2013 (Klinger).
Notice of Allowance issued Dec. 24, 2014 issued in Connection With U.S. Appl. No. 13/770,677, filed Feb. 19, 2013 (Klinger).
Mar. 20, 2015 Examiner's Report Issued in Connection With Australian Application No. 2013203367 (Klinger).
Jan. 15, 2015 Official Action Issued in Connection With Canadian Application No. 2,760,802, filed Aug. 19, 2012.
Response to the Jan. 15, 2015 Official Action Issued in Connection With Canadian Application No. 2,760,802, filed Aug. 19, 2012 (Klinger).
Sep. 23, 2014 Reply to Oppositions filed against EP2405739B in the name of Yeda Research Development Co Ltd. By Activis Group PTC ehf and others in connection with European Application No. 10810282.3 (Klinger).
Jun. 4, 2015 Amendment in Response to Jan. 7, 2014 Official Action filed in Connection With Japanese Application No. 2012-525530, filed Feb. 20, 2012 (Klinger) together with an English translation thereof.
Gibson (2004) "Selection of Injecting Volume", Pharmaceutical Preformulation and Formulation, p. 332.
Khan et al. (2009) "Glatiramer acetate 20mg subcutaneous twice-weekly versus daily injections: results of a pilot, prospective, randomised, and rater-blinded clinical and MRI 2-year study in relapsing-remitting multiple sclerosis" Immunomodulation—2; Friday, Sep. 11, 2009.
May 22, 2015 Office Action issued in connection with U.S. Appl. No. 14/673,257, filed Mar. 30, 2015 (Klinger).
Feb. 6, 2014 Opposition in connection with European Application No. 10810282.3; Patentee: Yeda Research and Development Co., Ltd. vs. Opponent: Synthon BV.
Feb. 7, 2014 Opposition in connection with European Application No. 10810282.3; Patentee: Yeda Research and Development Co., Ltd. vs. Opponent: Actavis Group ehf.
Notice of Opposition to a European patent together with the Statement of Grounds for Opposition filed Feb. 10, 2014 in connection with European Patent EP 2405749 B1; Patentee: Yeda Research and Development Co., Ltd. vs. Opponent Generics [UK] Limited (trading as Mylan).
Feb. 6, 2012 Office Action Issued in Connection With U.S. Appl. No. 12/806,684, filed Aug. 19, 2010 (Klinger).
Jun. 27, 2014 Summons to attend oral proceedings pursuant to Rule 115 (1) EPC in connection with European Patent Application No. 10160099.7.
Nov. 25, 2011 Examiner's Report Issued in Connection With Australian Application No. 2010284666, filed Aug. 19, 2012 (Klinger).
Response to the Nov. 25, 2011 Examiner's Report filed Oct. 15, 2012 in Connection With Australian Application No. 2010284666, filed Aug. 19, 2012 (Klinger).
Jul. 10, 2013 Official Action Issued in Connection With Canadian Application No. 2,760,802, filed Aug. 19, 2012 (Klinger).
Response to the Jul. 10, 2013 outstanding Examiner's Report filed Oct. 10, 2013 in connection with Canadian Application No. 2,760,802, filed Aug. 19, 2012 (Klinger).
Jan. 8, 2014 Official Action Issued in Connection With Canadian Application No. 2,760,802, filed Aug. 19, 2012 (Klinger).
Response to the Jan. 8, 2014 outstanding Examiner's Report filed Apr. 8, 2014 in connection with Canadian Application No. 2,760,802, filed Aug. 19, 2012 (Klinger).
Apr. 1, 2013 Official Action Issued in Connection With Chinese Application No. 201080036966.0, filed Feb. 20, 2012 (Klinger) and English Translation thereof.
Response to the Apr. 1, 2013 outstanding Official Action filed Jun. 28, 2013 in Connection With Chinese Application No. 201080036966.0, Feb. 20, 2012 (Klinger).
Aug. 9, 2013 Official Action Issued in Connection With Chinese Application No. 201080036966.0, filed Feb. 20, 2012 (Klinger) and English Translation thereof.
Response to the Aug. 9, 2013 outstanding Official Action filed Oct. 24, 2013 in Connection With Chinese Application No. 201080036966.0, Feb. 20, 2012 (Klinger).
Decision of Rejection Issued in Connection With Chinese Application No. 201080036966.0, issued Feb. 8, 2014.
Response to the Nov. 28, 2012 outstanding Official Action in connection with Eurasian patent application No. 201270292 (Klinger).
Official Action issued Mar. 18, 2013 in connection with Eurasian patent application No. 201270292 (Klinger) including English translation thereof.
Response to the Mar. 18, 2013 outstanding Official Action in connection with Eurasian patent application No. 201270292.
Official Action issued Aug. 14, 2013 in connection with Eurasian patent application No. 201270292.
Response to the Aug. 14, 2013 outstanding Official Action in connection with Eurasian patent application No. 201270292.
Jul. 1, 2009 Response to Final Office action in connection with U.S. Appl. No. 11/651,212.
Sep. 13, 2012 Response to Communication under Art 94 (3) EPC in connection with European Application No. 10810282.3.
Communication Pursuant to Rule 69 EPC issued Sep. 2, 2013 in connection with European Patent Application No. 13166080.5.
Extended European Search Report issued Jul. 30, 2013 in connection with European Patent Application No. 13166080.5.
Feb. 26, 2014 Response to Extended European Search Report issued Jul. 30, 2013 in connection with European Patent Application No. 13166080.5.
Jan. 7, 2014 Official Action Issued in Connection With Japanese Application No. 2012-525530, filed Feb. 20, 2012.
Sep. 17, 2013 Official Action Issued in Connection with Korean Application No. 10-2012-7007115.
Feb. 5, 2014 Decision of Rejection issued in Connection with Korean Application No. 10-2012-7007115.
Feb. 26, 2014 Office action Issued in Connection With Taiwanese Application No. 099128023, filed Aug. 20, 2010 including English translation thereof.
Preliminary Conclusion of Substantive Examination issued Nov. 8, 2012 in connection with Ukrainian patent application No. 2012 03259 including English translation thereof.
Immunological Responses to Different Doses of Glatiramer Acetate in MS: Analyses from the Forte Trial, Yong W. V., et al., poster session dated Apr. 28, 2009, presented at the 61st Annual American Academy of Neurology meeting in Seattle, Washington U.S.A.
Flechter S, et al. (2002) "Copolymer 1 (Glatiramer Acetate) in Relapsing Forms of Multiple Sclerosis: Open Multicenter Study of Alternate-Day Adlninistration". Clinical Neuropharmacology, 25: 11-15.
Khan O. et al., "A phase 3 trial to assess the efficacy and safety of glatiramer acetate injections 40mg administered 3 times a week compared to placebo" Oct. 13, 2012; European Committee for Treatment and Research in Multiple Sclerosis.
Cohen et al. (2007) "Randomized, double-blind, dose comparison study of glatiramer acetate in relapsing-remitting MS". Neurology, 68: 939-944.
Endo et al. (2004) "How to proceed with therapy of multiple sclerosis". Modern Physician, 24: 1896-1901 including English translation thereof.
"Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr.

(56) References Cited

OTHER PUBLICATIONS 2, 2013]. Retrieved from the Internet: <URL:www.tevapharm.com/Media/News/Pages/2012/1743500.aspx?year=2012& p.>.
Teva Provides Update on Forte Trial, published on Jul. 7, 2008 at Jerusalem, Israel by Teva Pharmaceutical Industries Ltd.
Copaxone 20 mg/ml, Solution for Injection, Pre-Filled Syringe, Summary of Product Characteristics updated on Apr. 17, 2009.
Copaxone 20 mg/ml or Copaxone 40 mg/ml, NDA 020622/S-089 FDA Approved Labeling Text dated Jan. 28, 2014.
Feb. 6, 2015 Petition for Inter Partes Review, filed in connection with *Mylan Pharmaceuticals Inc. v. Yeda Research & Development Co. Ltd.* For U.S. Pat. No. 8,232,250 in the United States Patent and Trademark Office Patent Trial and Appeal Board (Case No. IPR2015-00643).
Declaration of Stephen J. Peroutka, M.D., Ph.D., filed on Feb. 6, 2015 as Exhibit 1003 in connection with *Mylan Pharmaceuticals Inc. v. Yeda Research & Development Co. Ltd.* For U.S. Pat. No. 8,232,250 in the United States Patent and Trademark Office Patent Trial and Appeal Board (Case No. IPR2015-00643).
Expert Declaration of an Green, M.D. In Support of Petition for Inter Partes Review of U.S. Pat. No. 8,232,250, filed on Feb. 6, 2015 as Exhibit 1004 in connection with *Mylan Pharmaceuticals Inc. v. Yeda Research & Development Co. Ltd.* For U.S. Pat. No. 8,232,250 in the United States Patent and Trademark Office Patent Trial and Appeal Board (Case No. IPR2015-00643).
Feb. 7, 2015 Petition for Inter Partes Review filed in connection with *Mylan Pharmaceuticals Inc. v. Yeda Research & Development Co. Ltd.* For U.S. Pat. No. 8,399,413 in the United States Patent and Trademark Office Patent Trial and Appeal Board (Case No. IPR2015-00644).
Declaration of Stephen J. Peroutka, M.D., Ph.D., filed on Feb. 6, 2015 as Exhibit 1003 in connection with *Mylan Pharmaceuticals Inc. v. Yeda Research & Development Co. Ltd.* For U.S. Pat. No. 8,399,413 in the United States Patent and Trademark Office Patent Trial and Appeal Board (Case No. IPR2015-00644).
Expert Declaration of an Green, M.D. in Support of Petition for Inter Partes Review of U.S. Patent No. 8,399,413, filed on Feb. 6, 2015 as Exhibit 1004 in connection with *Mylan Pharmaceuticals Inc. v. Yeda Research & Development Co. Ltd.* for U.S. Patent No. 8,399,413 in the United States Patent and Trademark Office Patent Trial and Appeal Board (Case No. IPR2015-00644).
Mar. 3, 2015 Petition for Inter Partes Review, filed in connection with *Mylan Pharmaceuticals Inc. v. Yeda Research & Development Co. Ltd.* For U.S. Patent No. 8,969,302 in the United States Patent and Trademark Office Patent Trial and Appeal Board (Case No. IPR2015-00830).
Declaration of Stephen J. Peroutka, M.D., Ph.D., filed on Mar. 3, 2015 as Exhibit 1003 in connection with *Mylan Pharmaceuticals Inc. v. Yeda Research & Development Co. Ltd.* For U.S. Patent No. 8,969,302 in the United States Patent and Trademark Office Patent Trial and Appeal Board (Case No. IPR2015-00830).
Expert Declaration of Ari Green, M.D. in Support of Petition for Inter Partes Review of U.S. Patent No. 8,969,302, filed on Mar. 3, 2015 as Exhibit 1004 in connection with *Mylan Pharmaceuticals Inc. v. Yeda Research & Development Co. Ltd.* for U.S. Patent No. 8,969,302 in the United States Patent and Trademark Office Patent Trial and Appeal Board (Case No. IPR2015-00830).
Affidavit of Marlene S. Bobka dated Dec. 9, 2014 together with Exhibit A, submitted as Exhibit 1007 in Inter Partes Review Case Nos. IPR2015-00643, IPR2015-00644 and IPR2015-00830.
PCT International Application Publication No. WO 2007/081975, published Jul. 19, 2007 (Pinchasi), submitted as Exhibit 1005 in Inter Partes Review Case Nos. IPR2015-00643, IPR2015-00644 and IPR2015-00830.
Cohen et al., "Randomized, double-blind, dose comparison study of glatiramer acetate in relapsing-remitting MS". Neurology, 2007, 68: 939-944, submitted as Exhibit 1006 in Inter Partes Review Case Nos. IPR2015-00643, IPR2015-00644 and IRR2015-00830.
Flechter S, et al., "Copolymer 1 (Glatiramer Acetate) in Relapsing Forms of Multiple Sclerosis: Open Multicenter Study of Alternate-Day Adlninistration" Clinical Neuropharmacology, 2002, 25: 11-15, submitted as Exhibit 1008 in Inter Partes Review Case Nos. IPR2015-00643, IPR2015-00644 and IPR2015-00830.
Zeev Meiner et al., "Copolymer 1 in relapsing-remitting multiple sclerosis: a multi-centre trial" in: Abramsky et al., *Frontiers in Multiple Sclerosis: Clinical Research and Therapy* (London, Martin Dunitz, 1997), pp. 213-221, submitted as Exhibit 1009 in Inter Partes Review Case Nos. IPR2015-00643, IPR2015-00644 and IPR2015-00830.
Khan et al., "Randomized, prospective, rater-blinded, four-year, pilot study to compare the effect of daily versus every -other-day injections in relapsing-remitting multiple sclerosis" Mutt. Scler. 2008, 14 Suppl. 1 S296, submitted as Exhibit 1010 in Inter Partes Review Case Nos. IPR2015-00643, IPR2015-00644 and IPR2015-00830.
Caon et al., "Randomized, prospective, rater-blinded, four year pilot study to compare the effect of daily versus every other day glatiramer acetate 20 mg subcutaneous injections in RRMS" Neurology, 2009, vol. 72, No. 11, p. A317,submitted as Exhibit 1011 in Inter Partes Review Case Nos. IPR2015-00643, IPR2015-00644 and IPR2015-00830.
Flechter et al., "Comparison of glatiramer acetate (Copaxone®) and interferon $\beta$-1b (Betaferon®) in multiple sclerosis patients: an open-label 2-year follow up", 197 Journal of the Neurological Sciences, 51-55 (2002), submitted as Exhibit 1012 in Inter Partes Review Case Nos. IPR2015-00643, IPR2015-00644 and IPR2015-00830.
Miller, The importance of early diagnosis of multiple sclerosis, 10(3) (Suppl. S-b) J.Manag. Care Pharm., S4-11 (2004),submitted as Exhibit 1013 in Inter Partes Review Case Nos. IPR2015-00643, IPR2015-00644 and IPR2015-00830.
Bornstein, "Multiple Sclerosis: Trial of a Synthetic Polypeptide", 11:3 Annals of Neurology, 317-19 (1982), submitted as Exhibit 1014 in Inter Partes Review Case Nos. IPR2015-00643, IPR2015-00644 and IPR2015-00830.
Bornstein et al., "Clinical Trials of Copolymer I in Multiple Sclerosis", 436 Annals New York Academy of Sciences, 366-372 (1984), submitted as Exhibit 1015 in Inter Partes Review Case Nos. IPR2015-00643, IPR2015-00644 and IPR2015-00830.
Bornstein et al., "A Pilot Trial of Cop 1 in Exacerbating-Remitting Multiple Sclerosis", 317:7 The New England Journal of Medicine, 408-14 (1987), submitted as Exhibit 1016 in Inter Partes Review Case Nos. IPR2015-00643, IPR2015-00644 and IPR2015-00830.
Food and Drug Administration, *Guideline for Industry: Dose-Response Information to Support Drug Registration*, Federal Register vol. 59 (Nov. 9, 1994), pp. 55972-55976, submitted as Exhibit 1017 in Inter Partes Review Case Nos. IPR2015-00643, IPR2015-00644 and IPR2015-00830.
Johnson et al., "Copolymer 1 reduces relapse rate and improves disability in relapsing-remitting multiple sclerosis", 43 Neurology, 1268-1276 (1995), submitted as Exhibit 1018 in Inter Partes Review Case Nos. IPR2015-00643, IPR2015-00644 and IPR2015-00830.
Affidavit of Marlene S. Bobka dated Jan. 5, 2015, submitted as Exhibit 1019 in Inter Partes Review Case Nos. IPR2015-00643, IPR2015-00644 and IPR2015-00830.
Arnon, The Development of Cop 1(Copaxone®), An Innovative Drug for the Treatment of Multiple Sclerosis: Personal Reflections, 50 Immunology Letters 1-15 (1996), submitted as Exhibit 1020 in Inter Partes Review Case Nos. IPR2015-00643, IPR2015-00644 and IPR2015-00830.
Benet et al., "Pharmacokinetics: The Dynamics of Drug Absorption, Distribution, and Elimination" in: Goodman & Gilman, *The Pharmacological Basis of Therapeutics* (New York, McGraw-Hill, 1995), pp. 3-27, submitted as Exhibit 1021 in Inter Partes Review Case Nos. IPR2015-00643, IPR2015-00644 and IPR2015-00830.
Lobel et al., "Copolymer-1", 21(2) Drugs of the Future, 131-134 (1996), submitted as Exhibit 1022 in Inter Partes Review Case Nos. IPR2015-00643, IPR2015-00644 and IPR2015-00830.
Haines et al., Linkage of the MHC to Familial Multiple Sclerosis Suggests Genetic Heterogeneity. The Multiple Sclerosis Genetics Group, Hum.Mol. Genet. 7:1229-34 (Aug. 1998), submitted as Exhibit 1023 in Inter Partes Review Case Nos. IPR2015-00643, IPR2015- 00644 and 1PR2015-00830.

(56) References Cited

OTHER PUBLICATIONS

U.S. Pat. No. 6,342,476, issued Jan. 29, 2002 (Konfino, et al.), submitted as Exhibit 1024 in Inter Partes Review Case Nos. IPR2015-00643, IPR2015-00644 and IPR2015-00830.
Ge et al., Glatiramer Acetate (Copaxone) Treatment in Relapsing-Remitting MS: Quantitative MR Assessment, 54 Neurology, 813-17 (2000), submitted as Exhibit 1025 in Inter Partes Review Case Nos. IPR2015-00643, 1PR2015-00644 and IPR2015-00830.
Comi et al. "European/Canadian multicenter, double-blind, randomized, placebo-controlled study of the effects of glatiramer acetate on magnetic resonance imagine-measured disease activity and burden in patients with relapsing multiple sclerosis". Ann Neurol. 49:290-7 (2001), submitted as Exhibit 1026 in Inter Partes Review Case Nos. IPR2015-00643, IPR2015-00644 and IPR2015-00830.
Jean-Pierre Boissel et al. "Using pharmacokinetic-pharmacodynamic relationships to predict the effect of poor compliance," CLIN. PHARMACOL. 41:1-6 (2002), submitted as Exhibit 1027 in Inter Partes Review Case Nos. IPR2015-00643 and IPR2015-00643.
McDonald et al., Recommended Diagnostic Criteria for Multiple Sclerosis: Guidelines from the International Panel on the Diagnosis of Multiple Sclerosis, Ann. Neurol. 50:121-27 (2001), submitted as Exhibit 1027 in Inter Partes Review Case No. IPR2015-00830.
McBride, "Nonadherence to Immunomodulation in Multiple Sclerosis," abstract for Second International Multiple Sclerosis Week Multiple Sclerosis: A World View, a conference held on Jun. 5-9, 2002 at Chicago, Illinois, submitted as Exhibit 1028 in Inter Partes Review Case Nos. IPR2015-00643, IPR2015-00644 and IPR2015-00830.
Simpson et al., Adis Drug Evaluation—Glatiramer Acetate a Review of its use in Relapsing-Remitting Multiple Sclerosis, 16:12 CNS Drugs, 825-50, 834 (2002), submitted as Exhibit 1029 in Inter Partes Review Case Nos. IPR2015-00643, IPR2015-00644 and IPR2015-00830.
Edgar, et al., "Lipoatrophy in Patients with Multiple Sclerosis on Glatiramer Acetate", 31 Can. J. Neurol. Sci., 58-63 (2004), submitted as Exhibit 1030 in Inter Partes Review Case Nos. IPR2015-00643, IPR2015-00644 and IPR2015-00830.
Rich et al., Stepped-care approach to treating MS: A managed care treatment algorithm, J. Managed Care Pharm. 10:526-S32 (Jun. 2004), submitted as Exhibit 1031 in Inter Partes Review Case Nos. IPR2015-00643 and IPR2015-00643, and Exhibit 1058 in Inter Partes Review Case No. IPR2015-00830.
Ziemssen et al., Effects of Glatiramer Acetate on Fatigue and Days of Absence from Work in First-Time Treated Relapsing-Remitting Multiple Sclerosis, Hlth. &Qual. Life Outcomes 6:67 (2008), submitted as Exhibit 1045 in Inter Partes Review Case Nos. IPR2015-00643 and IPR2015-00643, and Exhibit 1031 in Inter Partes Review Case No. IPR2015-00830.
Stuart, Clinical Management of Multiple Sclerosis: The Treatment Paradigm and Issues of Patient Management, J. Managed Care Pharmacy 10:S19-S25 (Jun. 2004), submitted as Exhibit 1032 in Inter Partes Review Case Nos. IPR2015-00643, IPR2015-00644 and IPR2015-00830.
Bakshi et al., Imaging of Multiple Sclerosis: Role in Neurotherapeutics, 2(2) NEURORX, 277-303 (2005), submitted as Exhibit 1033 in Inter Partes Review Case Nos. IPR2015-00643, IPP2015-00644 and IPR2015-00830.
Beringer et al., "Clinical Pharmacokinetics and Pharmacodynamics", in *Remington: The Science and Practice of Pharmacy* (Philadelphia, Lippincott Williams & Wilkins, 2005), pp. 1191-1205, submitted as Exhibit 1034 in Inter Partes Review Case Nos. IPR2015-00643, IPR2015-00644 and IPR2015-00830.
Franklin et al., "Drug Absorption, Action, and Disposition", in *Remington: The Science and Practice of Pharmacy* (Philadelphia, Lippincott Williams & Wilkins, 2005), 1142-1170, submitted as Exhibit 1035 in Inter Partes Review Case Nos. IPR2015-00643, IPR2015-00644 and IPR2015-00830.
PCT International Application Publication No. WO 2005/120542, published Dec. 22, 2005 (Rasmussen), submitted as Exhibit 1036 in Inter Partes Review Case Nos. IPR2015-00643, IPR2015-00644 and 1PR2015-00830.
Devonshire et al., "The Global Adherence Project—A Multicentre Observational Study on Adherence to Disease-Modifying Therapies in Patients Suffering from Relapsing-Remitting Multiple Sclerosis", Multiple Sclerosis 12:S1 (P316), 2006 (abstract)[online], [retrieved on Nov. 18, 2014]. Retreived from the Internet <URL:msj.sagepub.com/content/12/1_suppl/S1.citation>, submitted as Exhibit 1037 in Inter Partes Review Case Nos. IPR2015-00643, IPR2015-00644 and 1PR2015-00830.
Ford et al., "A Prospective Open-Label Study of Glatiramer Acetate: Over a Decade of Continuous Use in Multiple Sclerosis Patients", 12 Multiple Sclerosis, 309-320 (2006), submitted as Exhibit 1038 in Inter Partes Review Case Nos. IPR2015-00643, 1PR2015-00644 and IPR2015-00830.
Frohman, Multiple Sclerosis—The Plaque and its Pathogenesis, New England J.Med. 354:942-55 (2006), submitted as Exhibit 1039 in Inter Partes Review Case Nos. IPR2015-00643, IPR2015-00644 and IPR2015-00830.
Kragt et al., How Similar are Commonly Combined Criteria for EDSS Progression in Multiple Sclerosis?, 12(6) Multiple Sclerosis 782-786 (2006), submitted as Exhibit 1040 in Inter Partes Review Case Nos. IPR2015-00643, IPR2015-00644 and IPR2015-00830.
Manso et al., "Life Cycle Management of Ageing Pharmaceutical Assets", 3:7 Pharmaceutical Law Insight, (2006), submitted as Exhibit 1041 in Inter Partes Review Case Nos. IPR2015-00643, IPR2015-00644 and IPR2015-00830.
Almeida et al., "Localized Panniculitis Secondary to Subcutaneous Glatiramer Acetate Injections for the Treatment of Multiple Sclerosis: A Clinicopathologic and Immunohistochemical Study", J. Am. Acad. Dermatol 55:968-74 (2006), submitted as Exhibit 1042 in Inter Partes Review Case Nos. IPR2015-00643, 1PR2015-00644 and IPR2015-00830.
Klauer and Zettl, "Compliance, Adherence and the Treatment of Multiple Sclerosis", J. Neurol. 255 [Suppl.6]:87-92 (2008), submitted as Exhibit 1043 in Inter Partes Review Case Nos. IPR2015-00643, 1PR2015-00644 and IPR2015-00830.
Pelidou at al., Multiple Sclerosis Presented as Clinically Isolated Syndrome: The Need for Early Diagnosis and Treatment, Ther. Clin. Riskmanagement 4:627-30 (Jun. 2008), submitted as Exhibit 1044 in Inter Partes Review Case Nos. IPR2015-00643.
Jacobs et al., Intramuscular interferon beta-1a therapy initiated during a first demyelinating event in multiple sclerosis, New Engl. J.Med. 343:898-904 (2008), submitted as Exhibit 1045 in Inter Partes Review Case No. IPR2015-00830.
Teva Provides Update on Forte Trial, published on Jul. 7, 2008 at Jerusalem, Israel by Teva Pharmaceutical Industries Ltd. submitted as Exhibit 1046 in Inter Partes Review Case Nos. IPR2015-00643, IPR2015-00644 and IPR2015-00830.
Copaxone®, Food and Drug Administration Approved Labeling, 2001 (NDA 20-622/S-015/S-015), submitted as Exhibit 1047 in Inter Partes Review Case Nos. IPR2015-00643, IPR2015-00644 and IPR2015-00830.
Betaseron® Interferon beta-1b, Product Label, 2003 (10004938), submitted as Exhibit 1048 in Inter Partes Review Case Nos. IPR2015-00643, IPR2015-00644 and IPR2015-00830.
Rebif® (interferon beta-1a), Product Label, 2003, submitted as Exhibit 1049 in Inter Partes Review Case Nos. IPR2015-00643.
Avonex® (interferon beta-1a) IM Injection, Product Label, 2006, submitted as Exhibit 1050 in Inter Partes Review Case Nos. IPR2015-00643, IPR2015-00644 and IPR2015-00830.
Tysabri®, Product Label, 2008, submitted as Exhibit 1051 in Inter Partes Review Case Nos. IPR2015-00643, IPR2015-00644 and IPR2015-00830.
Copaxone®, Food and Drug Administration Approved Labeling, Feb. 2009, submitted as Exhibit 1052 in Inter Partes Review Case Nos. IPR2015-00643, IPR2015-00644 and IPR2015-00830.
Extavia®, Abbreviated Drug Monograph: Interferon beta 1b (Extavia®), Sep. 2010, submitted as Exhibit 1053 in Inter Partes Review Case Nos. IPR2015-00643, IPR2015-00644 and IPR2015-00830.

(56) References Cited

OTHER PUBLICATIONS

Rebif® (interferon beta-1a), Product Label, Jun. 2005, submitted as Exhibit 1059 in IPR2015-00643, Exhibit 1060 in Inter Partes Review Case No. IPR2015-00644 and Exhibit 1054 in Inter Partes Review Case No. IPR2015-00830.
Jacobs et al., (2000) "Intramuscular interferon beta-1a therapy initiated during a first demyelinating . . . " The New England Journal of Medicine, vol. 343, No. 13, pp. 898-904, submitted as Exhibit 1054 in Inter Partes Review Case Nos. IPR2015-00643 and IPR2015-00644.
Stedman's Medical Dictionary for Health Professionals and Nursing, sixth edition (2008), submitted as Exhibit 1055 in Inter Partes Review Case Nos. IPR2015-00643 and IPR2015-00644.
U.S. Pat. No. 3,849,550, issued Nov. 19, 1974 (Teitelbaum et al.), submitted as Exhibit 1055 in Inter Partes Review Case Nos. IPR2015-00643 and 1PR2015-00644.
U.S. Patent Application Publication No. US 2009-0149541 A1, published Jun. 11, 2009 (Stark et al.), submitted as Exhibit 1056 in Inter Partes Review Case Nos. IPR2015-00643 and IPR2015-00644 and 1PR2015-00830.
Copaxone®, Food and Drug Administration Approved Labeling, Jan. 2014, submitted as Exhibit 1057 in Inter Partes Review Case No. IPR2015-00643.
DiPiro et al., Concepts in clinical pharmacokinetics, Fifth Edition, in Introduction to Pharmacokinetics and Pharmacodynamics, American Society of Health-System Pharmacists® (2010), submitted as Exhibit 1062 in IPR2015-00643, and Exhibit 1057 in Inter Partes Review Case Nos. IPR2015-00644 and IPR2015-00830.
Thixia, "Copaxone". In Multiple Sclerosis All about MS [online], Apr. 11, 2008 [retrieved on Feb. 5, 2015]. Retrieved from the Internet: <URL:scamparoo.wordpress.com/2008/04/11/ms-therapies-copaxone/>, submitted as Exhibit 1058 in Inter Partes Review Case No. IPR2015-00643, and Exhibit 1062 in Inter Partes Review Case Nos. IPR2015-00644.
M. Tintore et al., Baseline MRI predicts future attacks and disability in clinically isolated syndromes, 67 Neurology 968-972, (2006), submitted as Exhibit 1058 in Inter Partes Review Case No. IPR2015-00644.
Guidance for Industry Population Pharmacokinetics [online]. Food and Drug Administration, Feb. 1999 [retrieved on Jun. 23, 2015]. Retrieved from the Internet: <URL:www.fda.gov/downloads/Drugs/Guidances/UCM072137.pdf>, submitted as Exhibit 1063 in IPR2015-00643 and Exhibit 1059 in Inter Partes Review Case Nos. IPR2015-00644 and IPR2015-00830.
U.S. Patent Application Publication No. US 2013-0165387 A1, published Jun. 27, 2013 (Klinger), submitted as Exhibit 1060 in Inter Partes Review Case Nos. IPR2015-00830.
Orange Book: Approved Drug Products with Therapeutic Equivalence Evaluations [online], accessdata.fda.gov [retrieved on Jan. 29, 2015]. Retrieved from the Internet: <URL://www.accessdata.fda.gov/scripts/cder/ob/docs/patexclnew.cfm?Appl_No=020622&Product_No=003&table1=OB_Rx>, submitted as Exhibit 1060 in Inter Partes Review Case No. IPR2015-00643 and Exhibit 1061 in Inter Partes Review Case No. IPR2015-00644.
P.M. Rothwell et al. Doctors and Patients don't agree: cross sectional study of patients' and doctors ' perceptions and assessments of disability in multiple sclerosis 314 The BMJ 1580 (May 31, 1997), submitted as Exhibit 1061 in Inter Partes Review Case No. IPR2015-00643.
Amendment in Response to Feb. 14, 2012 Office Action and Summary of May 8, 2012 Examiner Interview Pursuant to 37 C.F.R. § 1.133(b), filed in connection with U.S. Appl. No. 13/308,299, submitted as Exhibit 1064 in Inter Partes Review Case No. IPR2015-00643.
U.S. Appl. No. 12/231,292, filed Aug. 29, 2008 (Aharoni et al.).
U.S. Appl. No. 13/083,112, filed Apr. 8, 2011 (Klinger).
U.S. Appl. No. 11/651,212, filed Jan. 9, 2007 (Pinchasi). The specification and claims as originally filed.
U.S. Appl. No. 12/861,655, filed Aug. 23, 2010 (Stark et al.).
U.S. Appl. No. 12/761,367, filed Apr. 15, 2010 (Altman et al.).
U.S. Appl. No. 12/785,125, filed May 21, 2010 (Altman et al.).
U.S. Appl. No. 13/384,021, filed Jul. 14, 2010 (Altman et al.).
U.S. Appl. No. 12/806,684, filed Aug. 19, 2010 (Klinger).
Office Action issued Jul. 20, 2009 in connection with U.S. Appl. No. 11/651,212, filed Jan. 9, 2007.
Amendment filed Jul. 1, 2009 in connection with U.S. Appl. No. 11/651,212, filed Jan. 9, 2007.
Office Action issued Apr. 2, 2009 in connection with U.S. Appl. No. 11/651,212, filed Jan. 9, 2007.
Amendment filed Dec. 22, 2008 in connection with U.S. Appl. No. 11/651,212, filed Jan. 9, 2007.
Office Action issued Jun. 20, 2008 in connection with U.S. Appl. No. 11/651,212, filed Jan. 9, 2007.
Written Opinion of the International Searching Authority issued Oct. 5, 2007 in connection with PCT International Application No. PCT/US07/00575, filed Jan. 9, 2007.
PCT International Search Report issued Oct. 5, 2007 in connection with PCT International Application No. PCT/US07/00575, filed Jan. 9, 2007.
Response filed Sep. 23, 2010 in connection with U.S. Appl. No. 12/785,125, filed May 21, 2010.
Office Action issued Aug. 24, 2010 in connection with U.S. Appl. No. 12/785,125, filed May 21, 2010.
Aug. 19, 2013 Reply to Notice of Opposition, filed in connection with European Patent No. EP2275086.
Jul. 15, 2014 Notice of Withdrawal of Opposition, filed in connection with European Patent No. EP2275086.
Dec. 11, 2012 Notice of Opposition, filed in connection with European Patent No. EP2275086.
Communication issued Jul. 29, 2010 in connection with EPO Application No. 10160099.7.
Response filed Dec. 17, 2010 in connection with European Patent Application No. 10160099.7.
Communication Pursuant to Article 94(3) EPC issued Feb. 11, 2011 in connection with European Patent Application No. 10160099.7.
Response filed Jun. 13, 2011 in connection with European Patent Application No. 10160099.
Written Opinion of the International Searching Authority issued Jun. 9, 2011, in connection with PCT International Application No. PCT/US2010/001972, filed Jul. 14, 2010.
PCT International Search Report issued Jun. 9, 2011 in connection with PCT International Application No. PCT/US2010/001972, filed Jul. 14, 2010.
Oct. 10, 2012 Office Action Issued in Connection With U.S. Appl. No. 12/806,684, filed Aug. 19, 2010.
Response to the Oct. 10, 2012 Office Action filed Jan. 10, 2013 in connection with U.S. Appl. No. 12/806,684, filed Aug. 19, 2010.
Jan. 17, 2013 Notice of Allowance issued in connection with U.S. Appl. No. 12/806,684, filed Aug. 19, 2010.
Issue Notification issued Feb. 27, 2013 in connection with U.S. Appl. No. 12/806,684, filed Aug. 19, 2010.
U.S. Appl. No. 13/308,299, filed Nov. 30, 2011 (Klinger).
Feb. 14, 2012 Office Action Issued in Connection With U.S. Appl. No. 13/308,299, filed Nov. 30, 2011 (Klinger).
Amendment in Response to Feb. 14, 2012 Office Action filed May 14, 2012 in connection with U.S. Appl. No. 13/308,299, filed Nov. 30, 2011 (Klinger).
Notice of Allowance issued Jun. 15, 2012 issued in Connection With U.S. Appl. No. 13/308,299, filed Nov. 30, 2011.
Issue Notification issued Jul. 11, 2012 issued in Connection With U.S. Appl. No. 13/308,299, filed Nov. 30, 2011.
International Search Report issued Oct. 4, 2010 in connection with PCT International Application No. PCT/US/10/02283, filed Aug. 19, 2010 (Klinger).
Written Opinion of the International Searching Authority issued Oct. 4, 2010 in connection with PCT International Application No. PCT/US/10/02283, filed Aug. 19, 2010 (Klinger).
Feb. 29, 2012 Official Action Issued in Connection With Canadian Application No. 2,760,802, filed Aug. 19, 2012. (Klinger).
Response to the Feb. 29, 2012 outstanding Examiner's Report filed May 29, 2012 in connection with Canadian Application No. 2,760,802, filed Aug. 19, 2012 (Klinger).

(56) References Cited

OTHER PUBLICATIONS

Jul. 24, 2012 Official Action Issued in Connection With Canadian Application No. 2,760,802, filed Aug. 19, 2012 (Klinger).
Response to the Jul. 24, 2012 outstanding Examiner's Report filed Oct. 24, 2012 in connection with Canadian Application No. 2,760,802, filed Aug. 19, 2012 (Klinger).
Official Action issued Nov. 28, 2012 in connection with Eurasian patent application No. 201270292 including English translation thereof.
Supplementary European Search Report issued Jul. 13, 2012 in connection with European Patent Application No. 10810282.3 filed Oct. 11, 2011.
Communication Pursuant to Article 94(3) EPC issued Aug. 8, 2012 in connection with European Patent Application No. 10810282.3, filed Oct. 11, 2011.
Response to Aug. 8, 2012 Communication Pursuant to Article 94(3) EPC filed Sep. 13, 2012 in connection with European Patent Application No. 10810282.3, filed Oct. 11, 2011.
Examination Report issued Nov. 5, 2012 in connection with New Zealand patent application No. 598661.
Anderson, et al. "Injection pain decreases with new 0.5 mL formulation of glatiramer acetate" The Consortium of Multiple Sclerosis Centers 2010 Annual Meeting, Jun. 2-5, 2010, San Antoinio, Texas (Abstract only).
Anderson, et al. (1992) "Revised estimate of the prevalence of multiple sclerosis in the United States". Ann Neurol. 31:333-36.
Arnon and Aharoni (2007) "Neurogenesis and neuroprotection in the CAN—Fundamental elements in the effect of glatiramer acetate on treatment of autoimmune neurological disorders". Mol Neurobiol. 36:245-53.
Bjartmar C, et al. (2002) "Pathological mechanisms and disease progression of multiple sclerosis: therapeutic implications". Drugs of Today. 38:7-29.
Bornstein, et al., "A Placebo-controlled, Double-blind, Randomized Two-center, Pilot Trial of Cop 1 in Chronic Prgressive Multiple Sclerosis," Neurol., 1991, 41, 533-539.
Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].
Bornstein "Clincal Experience: Hopeful Prospects in Multiple Sclerosis," Hospital Practice (Off. Ed.), 1992, vol. 27, No. 5, pp. L135-158, 141-142, 145-158.
Bornstein "Cop 1 may be Beneficial for Patients with Exacerbating-remitting Form of Multiple Sclerosis," Adv. Ther. (USA), 1987, 4, 206 (Abstract).
Bornstein et al., "Treatment of Multiple Sclerosis with Copolymer 1" In Treatment of Multiple Sclerosis: Trial Design, Results and Future Perspectives (Rudick R.A. & Goodkin D.E., eds., Springer Lerlag, London, 1992) 173-198.
Bornstein et al., "A Pilot Trial of Cop 1 in Exacerbating-remitting Multiple Sclerosis," New Eng. J. Med., 1987, 317(7), 408-414.
Bornstein et al., "Clinical Experience with COP-1 in Multiple Sclerosis," Neurol., 1988, 38(Suppl. 2) 66-69.
Bornstein et al., "Clinical Trials of a Synthetic Polypeptide (Copolymer 1) for the treatment of Mutliple Sclerosis" in Gonsett et al., Immunological and Clinical Aspects of Multiple Sclerosis (MTP Press, The Hague, 1984) 144-150.
Bornstein et al., "Clinical Trials of Copolymer 1 in Multiple Sclerosis," Ann. N.Y. Acad. Sci. (USA), 1984, 366-372.
Bornstein et al., "Multiple Sclerosis: Clinical Trials of a Synthetic Polypeptide, Copolymer 1," Neurol., 1985, 35, (Suppl. 1), 103 (Abstract).
Bornstein et al., "Multiple Sclerosis: Trial of a Synthetic Polypeptide," Ann. Neurol., 1982, 11, 317-319.
Bornstein et al., "Pilot Trial of COP-1 in Chronic Progressive Multiple Sclerosis: Preliminary Report," from the International Multiple Sclerosis Conference: An Update on Multiple Sclerosis, Roma (Italy), Sep. 15-17, 1988, in Elsevier Science Publisher, 1989, 225-232.

Bornstein et al., "Treatments of Multiple Sclerosis with a Synthetic Polypeptide: Preliminary Results," Ann. Neurol., 1980, 8, 117 (Abstract).
Bornstein et al., "Treatments of Multiple Sclerosis with a Synthetic Polypeptide: Preliminary Results," Trans. Am. Neurol. Assoc., 1980, 105, 348-350.
Bornstein et. al., "Clinical Trials of Cop 1 in Multiple Sclerosis," in Handbook of Multiple Sclerosis (S.D. Cook Marcel Rekker, ed., 1990) 469-480.
Brazeau GA, et al. (1998) "Current perspectives on pain upon injection of drugs". J Pharmaceutical Sci.(87)6:667-677.
Caon et al. (2009) "Randomized, prospective, rater-blinded, four year pilot study to compare the effect of daily versus every other day glatiramer acetate 20 mg subcutaneous injections in RRMS" Neurology vol. 72, No. 11, p. A317.
Chantelau, et al. (1991) "What make insulin injections painful?" BMJ. 303:26-27.
Comi G. "Treatment with glatiramer acetate delays conversion to clinically definite multiple sclerosis (CDMS) in patients with clinically isolated syndromes (CIS)". Program and abstracts of the American Academy of Neurology 60th Annual Meeting; Apr. 12-19, 2008; Chicago, Illinois. LBS.003.
Comi, et al. (2001) "European/Canadian multicenter, double-blind, randomized, placebo-controlled study of the effects of glatiramer acetate on magnetic resonance imagine-measured disease activity and burden in patients with relapsing multiple sclerosis". Ann Neurol. 49:290-7.
Comi, et al. (2008) "Results from a phase III, one-year, randomized, double-blind, parallel-group, dose-comparison study with glatiramer acetate in relapsing-remitting multiple sclerosis". Mult Soler. 14(suppl 1):S299.
Dhib-Jalbut S. (2002) "Mechanisms of action of interferons and glatiramer acetate in multiple sclerosis". Neurology. 58(Suppl 4):S3-S9.
Dhib-Jalbut S. (2003) "Glatiramer acetate (Copaxone) therapy for multiple sclerosis". Pharmacol Ther. 98:245-55.
Flechter S. et al. (2002) "Comparison of glatiramer acetate (Copaxone®) and interferon beta-1b (Betaferon®) in multiple sclerosis patients: An open-label 2-year follow up" Journal of the Neurological Sciences vol. 197, No. 1-2 pp. 51-55.
Frenken LA, et al. (1994) "Analysis of the efficacy of measures to reduce pain after subcutaneous administration of epoetin alfa". Nephrol Dial Transplant. 9: 1295-1298.
Guideline of Clinical investigation of medicinal products for the treatment of multiple sclerosis EMEA, London Nov. 16, 2006 CPMP/EWP/561/98 Rev.1, pp. 1-12.
Johnson, et al. (1998) "Extended use of glatiramer acetate (Copaxone) is well tolerated and maintains its clinical effect on multiple sclerosis relapse rate and degree of disability". Neurology. 50:701-8.
Jorgensen J.T. et al. (1996) "Pain assessment of subcutaneous injections" Annals of Pharmacotherapy, Harvey Whitney Books Company, vol. 30. No. 7-8, pp. 729-732.
Kansara, et al. (2009) "Subcutaneous Delivery". Drug Deliv Technol. Jun. 2009; 9(6):38-42.
Khan et al. (2008) "Randomized, prospective, rater-blinded, four-year, pilot study to compare the effect of daily versus every—other—day injections in relapsing—remitting multiple" Mult. Scler. 14 Suppl. 1 S296.
Khan O. et al., (2008) "Randomized, prospective, rater-blinded, four-year, pilot study to compare the effect of daily versus every-other-day glatiramer acetate 20 mg subcutaneous injections in relapsing-remitting multiple sclerosis", Multiple Sclerosis; 14: 5295-5298.
Medical News Today. Jul. 8, 2008. Web. Sep. 9, 2010. http://www.medicalnewstoday.com/articles/114183.php.
Miller D, et al. (2005) "Clinically isolated syndromes suggestive of multiple sclerosis, part I: natural history, pathogenesis, diagnosis, and prognosis". Lancet Neurol. 4(5):281-288.
Miller D, et al. (2005) "Clinically isolated syndromes suggestive of multiple sclerosis, part II: non-conventional MRI, recovery process, and management". Lancet Neurol. 4(6):341-348.

(56) References Cited

OTHER PUBLICATIONS

Neuhaus O, et al. (2003) "Immunomodulation in multiple sclerosis: from immunosuppression to neuroprotection". Trends Pharmacol Sci. 24:131-138.

Noseworthy, et al. (2000) "Multiple sclerosis". N Engl J Med. 343:938-52.

Polin. (2003) The Ins and Outs of Prefilled Syringes. Pharmaceutical & Medical Packaging News/Medical Device Link.

Polman, et al. (2005) "Diagnostic Criteria for Multiple Sclerosis: 2005 Revisions to the "McDonald" Criteria". Ann Neurol. 58:840-846.

Product Monograph, Copaxone, Revised Apr. 2, 2010: 1-35.

Ruggiere, et al. (2007) "Glatiramer acetate in multiple sclerosis: A review". CNS Drug Reviews. 13(2):178-91.

Schrempf W, et al. (2007) "Glatiramer acetate: Mechanisms of action in multiple sclerosis". Autoimmunity Reviews 2007. 6:469-475.

Shire, et al. (2004) "Challenges in the Development of High Protein Concentration Formulations". J Pharm Sci. 93(6):1390-1402.

Simpson Dene et al. (2002) "Glatiramer acetate: A review of its use in relapsing-remitting multiple sclerosis" CNS Drugs vol. 16, No. 12 pp. 825-850.

The National MS Society (USA) [cited Feb. 5, 2010]. Available from: http://www.nationalmssociety.org/about-multiple-sclerosis/what-we-know-about-ms/treatments/index.aspx.

Thrower BW. (2007) "Clinically isolated syndromes. Predicting and delaying multiple sclerosis". Neurology. 68 (Suppl 4):S12-S15.

Tselis, et al. (2007) "Glatiramer acetate in the treatment of multiple sclerosis". Neuropsychiatric Dis Treat. 3(2):259-67.

Van Metre Te, et al. (1996) "Pain and dermal reaction caused by injected glycerin in immunotherapy solutions". J Allergy Clin Immunol. 97:1033-9.

Weber, et al. (2007) "Mechanism of action of glatiramer acetate in treatment of multiple sclerosis". Neurotherapeutics. 4 (4) :647-53.

Wolinsky, et al. (2007) "Glatiramer acetate in primary progressive multiple sclerosis: Results of a multinational, multicenter, double-blind, placebo-controlled trial". Ann Neurol. 61:14-24.

Wolinsky, JS (2006) "The use of glatiramer acetate in the treatment of multiple sclerosis". Adv Neurol. 273-92.

Ziemssen and Schrempf (2007) "Glatiramer acetate: Mechanisms of action in multiple sclerosis". International Rev of Neurobiol. 79:537-70.

Aug. 25, 2015 Decision on Institution of Inter Partes Review, entered in connection with Mylan Pharmaceuticals Inc. v. Yeda Research & Development Co. Ltd. for U.S. Appl. No. 8,232,250 in the United States Patent and Trademark Office Patent Trial and Appeal Board (Case No. IPR2015-00644).

Aug. 25, 2015 Decision on Institution of Inter Partes Review, entered in connection Mylan Pharmaceuticals Inc. v. Yeda Research & Development Co. Ltd. for U.S. Appl. No. 8,399,413 in the United States Patent and Trademark Office Patent Trial and Appeal Board (Case No. IPR2015-00644).

Sep. 1, 2015 Decision on Institution of Inter Partes Review, entered in connection with Mylan Pharmaceuticals Inc. v. Yeda Research & Development Co. Ltd. for U.S. Appl. No. 8,969,302 in the United States Patent and Trademark Office Patent Trial and Appeal Board (Case No. IPR2015-00830).

\* cited by examiner

LOW FREQUENCY GLATIRAMER ACETATE THERAPY

This application is a continuation of U.S. Ser. No. 14/630,326, filed Feb. 24, 2015, which is a continuation of U.S. Ser. No. 13/770,677, filed Feb. 19, 2013, now U.S. Pat. No. 8,969,302, which is a continuation of U.S. Ser. No. 12/806,684, filed Aug. 19, 2010, now U.S. Pat. No. 8,399,413, which claims the benefit of U.S. Provisional Applications Nos. 61/337,612, filed Feb. 11, 2010 and 61/274,687, filed Aug. 20, 2009, the contents of all of which are hereby incorporated by reference in their entirety.

Throughout this application various publications are referenced by their full citations. The disclosures of these publications in their entireties are hereby incorporated by reference into this application in order to more fully describe the state of the art to which this invention pertains.

BACKGROUND OF THE INVENTION

Multiple Sclerosis (MS) is a chronic, debilitating disease of the central nervous system (CNS). MS has also been classified as an autoimmune disease. MS disease activity can be monitored by magnetic resonance imaging (MRI) of the brain, accumulation of disability, as well as rate and severity of relapses.

There are five main forms of multiple sclerosis:
1) Benign Multiple Sclerosis:

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.
2) Relapsing-Remitting Multiple Sclerosis (RRMS):

Patients suffering from RRMS experience sporadic exacerbations or relapses, as well as periods of remission. Lesions and evidence of axonal loss may or may not be visible on MRI for patients with RRMS.
3) Secondary Progressive Multiple Sclerosis (SPMS):

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.
4) Primary Progressive Multiple Sclerosis (PPMS);

PPMS is characterized by a steady progression of increasing neurological deficits without distinct attacks or remissions. Cerebral lesions, diffuse spinal cord damage and evidence of axonal loss are evident on the MRI of patients with PPMS.
5) Progressive-Relapsing Multiple Sclerosis (PRMS):

PRMS has periods of acute exacerbations while proceeding along a course of increasing neurological deficits without remissions. Lesions are evident on MRI of patients suffering from PRMS (Multiple sclerosis: its diagnosis, symptoms, types and stages, 2003, albany.net/.about.tjc/multiple-sclerosis.html; What are the Types of Multiple Sclerosis?, 2005, <imaginis.com/multiple-sclerosis/types-of-ms.asp?mode=1>).

Chronic progressive multiple sclerosis is a term used to collectively refer to SPMS, PPMS, and PRMS (Types of Multiple Sclerosis (MS), 2005, <themcfox.com/multiple-sclerosis/types-of-ms/types-of-multi-ple-sclerosis.htm>). The relapsing forms of multiple sclerosis are SPMS with superimposed relapses, RRMS and PRMS.

Glatiramer acetate (GA), a mixture of polypeptides which do not all have the same amino acid sequence, is marketed under the tradename Copaxone®. GA comprises the acetate salts of polypeptides containing L-glutamic acid, L-alanine, L-tyrosine and L-lysine at average molar fractions of 0.141, 0.427, 0.095 and 0.338, respectively. The average molecular weight of Copaxone® is between 5,000 and 9,000 daltons. ("Copaxone", Physician's Desk Reference, (2005), Medical Economics Co., Inc., (Montvale, N.J.), 3115.) Chemically, glatiramer acetate is designated L-glutamic acid polymer with L-alanine, L-lysine, L-tyrosine, acetate (salt).

Its structural formula is:

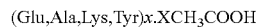

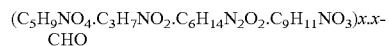

CAS-147245-92-9

Copaxone® ("Copaxone", Full Prescribing Information, (February, 2009), FDA Marketing. Label) (20 mg glatiramer acetate daily injection) is an approved therapy for patients with relapsing remitting multiple sclerosis (RRMS), including patients who have experienced a first clinical episode and have MRI features consistent with multiple sclerosis.

GA has also been disclosed for use in the treatment of other autoimmune diseases (U.S. Patent Publication No. 2002/0055466 A1 (R. Aharoni at al.), inflammatory non-autoimmune diseases (U.S. Patent Publication No. 2005/0014694 A1 (V. Wee Yong et al.); and U.S. Patent Application No. 2002/0077278 A1, published Jun. 20, 2002 (Young et al.)) and other diseases (U.S. Patent Publication Nos. 2003/0004099 A1 and 2002/0037848 A1 (Eisenbach-Schwartz, et al.); U.S. Pat. No. 6,514,938B1, issued Feb. 4, 2003 (Gad et al.); PCT International Publication No. WO 01/60392, published Aug. 23, 2001 (Gilbert at al.); PCT International. Publication No. WO 00/27417, published May 19, 2000 (Aharoni et al.); and PCT International Publication No. WO 01/97846, published Dec. 27, 2001 (Moses at al.).

The 20 mg/day subcutaneous (s.c.) dose has been shown to reduce the total number of enhancing lesions in MS patients as measured by MRI (G. Comi et al., European/Canadian Multicenter, Double-Blind, Randomized, Placebo-Controlled Study of the Effects of Glatiramer Acetere on Magnetic Resonance Imaging-Measured Disease Activity and Burden in Patients with Relapsing Multiple Sclerosis, Ann. Neurol. 49:290-297 (2001)).

Safety data accumulated for GA in clinical trials shows that the drug product is safe and well tolerated.

Disclosed is an effective low frequency dosage regimen of GA administration to patients suffering from a relapsing form of multiple sclerosis, including patients who have experienced a first clinical episode and have MRI features consistent with multiple sclerosis.

SUMMARY OF THE INVENTION

This invention provides a method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

This invention also provides a method of increasing the tolerability of GA treatment in a human patient suffering from relapsing-remitting multiple sclerosis or a patient who has experienced a first clinical episode and is determined to be at high risk of developing clinically definite multiple sclerosis which comprises reducing the frequency of subcutaneous injections of a pharmaceutical composition comprising a therapeutically effective dose of glatiramer acetate to three times over a period of seven days with at least one day between every injection.

In another embodiment, the therapeutically effective dose of glatiramer acetate is 40 mg/ml.

This invention also provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention additionally provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention yet also provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention further provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention provides glatiramer acetate for use in treating relapsing-remitting multiple sclerosis in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

This invention also provides glatiramer acetate for use in increasing the tolerability of GA treatment in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

DETAILED DESCRIPTION OF THE INVENTION

This invention provides a method of alleviating a symptom of relapsing-remitting multiple sclerosis in a human patient suffering from relapsing-remitting multiple sclerosis or a patient who has experienced a first clinical episode and is determined to be at high risk of developing clinically definite multiple sclerosis comprising administering to the human patient three subcutaneous injections of a therapeutically effective dose of glatiramer acetate over a period of seven days with at least one day between every subcutaneous injection so as to thereby alleviate the symptom of the patient.

In another embodiment, there are three injections for every seven days and there must be at least one day between each injection. In a further embodiment, possible injection schedules include Day 1, Day 3, Day 5; Day 1, Day 3, Day 6; Day 1, Day 3, Day 7; Day 1, Day 4, Day 6; Day 1, Day 4, Day 7; Day 1, Day 5, Day 7; Day 2, Day 4, Day 6; Day 2, Day 4, Day 7; Day 2, Day 5, Day 7; or Day 3, Day 5, Day 7.

In an embodiment, alleviating a symptom comprises reducing the frequency of relapses.

In yet another embodiment, alleviating a symptom comprises reducing the mean cumulative number of Gd-enhancing lesions in the brain of the patient.

In another embodiment, alleviating a symptom comprises reducing the mean number of new $T_2$ lesions in the brain of the patient.

In a further embodiment, alleviating a symptom comprises reducing the cumulative number of enhancing lesions on $T_1$-weighted images in the patient.

In another embodiment, alleviating a symptom comprises reducing brain atrophy in the patient.

In another embodiment, alleviating a symptom comprises increasing the time to a confirmed relapse in the patient.

In another embodiment, alleviating a symptom comprises reducing the total number of confirmed relapses in the patient.

In another embodiment, alleviating a symptom comprises reducing the progression of MRI-monitored disease activity in the patient.

In another embodiment, alleviating a symptom comprises reducing total volume of $T_2$ lesions in the patient.

In another embodiment, alleviating a symptom comprises reducing the number of new hypointense lesions on enhanced $T_1$ scans in the patient.

In another embodiment, alleviating a symptom comprises reducing the total volume of hypointense lesions on enhanced $T_1$ scans in the patient.

In another embodiment, alleviating a symptom comprises reducing the level of disability as measured by EDSS Score in the patient.

In another embodiment, alleviating a symptom comprises reducing the change in EDSS Score in the patient.

In another embodiment, alleviating a symptom comprises reducing the change in Ambulation Index in the patient.

In another embodiment, alleviating a symptom comprises reducing the level of disability as measured by EuroQoL (EQ5D) questionnaire in the patient.

In another embodiment, alleviating a symptom comprises reducing the level of disability as measured by the work productivity and activities impairment-General Health (WPAI-GH) questionnaire in the patient.

In an additional embodiment, the pharmaceutical composition is in a prefilled syringe for self administration by the patient.

In yet another embodiment, the therapeutically effective dose of glatiramer acetate is 40 mg/ml. In a further embodiment, the therapeutically effective dose of glatiramer acetate is 40 mg/0.75 ml.

In a further embodiment, the patient has not received glatiramer acetate therapy prior to initiation of the subcutaneous injections.

In an embodiment, the pharmaceutical composition is in the form of a sterile solution.

In another embodiment, the pharmaceutical composition further comprises mannitol.

In yet another embodiment, the pharmaceutical composition has a pH in the range of 5.5 to 8.5.

In an embodiment, the pharmaceutical composition has a pH in the range of 5.5 to 7.0.

In an embodiment the frequency of an immediate post injection reaction or the frequency of an injection site reaction is reduced relative to daily subcutaneous administration of 20 mg glatiramer acetate.

This invention also provides a method of increasing the tolerability of GA treatment in a human patient suffering from relapsing-remitting multiple sclerosis or a patient who has experienced a first clinical episode and is determined to be at high risk of developing clinically definite multiple sclerosis which comprises reducing the frequency of subcutaneous injections of a pharmaceutical composition comprising a therapeutically effective dose of glatiramer acetate to three times over a period of seven days with at least one day between every injection.

In another embodiment, increasing the tolerability of GA treatment in the human patient suffering from a relapsing form of multiple sclerosis comprises reducing the frequency of an immediate post injection reaction.

In yet another embodiment, the immediate post injection reaction is palpitations, feeling hot, flushing, hot flushes, tachycardia, dyspnoea, chest discomfort, chest pain, noncardiac chest, asthenia, back pain, bacterial infection, chills, cyst, face edema, fever, flu syndrome, infection, injection site erythema, injection site hemorrhage, injection site induration, injection site inflammation, injection site mass, injection site pain, injection site pruritus, injection site urticaria, injection site welt, neck pain, pain, migraine, syncope, tachycardia, vasodilatation, anorexia, diarrhea, gastroenteritis, gastrointestinal disorder, nausea, vomiting, ecchymosis, peripheral edema, arthralgia, agitation, anxiety, confusion, foot drop, hypertonia, nervousness, nystagmus, speech disorder, tremor, vertigo, bronchitis, dyspnea, laryngismus, rhinitis, erythema, herpes simplex, pruritus, rash, skin nodule, sweating, urticaria, ear pain, eye disorder, dysmenorrheal, urinary urgency, or vaginal moniliasis.

In an additional embodiment, increasing the tolerability of GA treatment in the human patient suffering from a relapsing form of multiple sclerosis comprises reducing the frequency of an injection site reaction.

In a further embodiment, the injection site reaction is erythema, hemorrhage, induration, inflammation, mass, pain, pruritus, urticaria, or welt that occurs immediately around the site of injection.

In an embodiment, a single clinical attack includes a clinical episode of optic neuritis, blurring of vision, diplopia, involuntary rapid eye movement, blindness, loss of balance, tremors, ataxia, vertigo, clumsiness of a limb, lack of coordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

In another embodiment, prior to administration the patient has at least 1 cerebral lesion detectable by an MRI scan and suggestive of multiple sclerosis.

In yet another embodiment, the lesion is associated with brain tissue inflammation, myelin sheath damage or axonal damage.

In an additional embodiment, the lesion is a demyelinating white matter lesion visible on brain MRI.

In a further embodiment, the white matter lesions are at least 3 mm in diameter.

This invention also provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention additionally provides a use of glatiramer acetate in the preparation of a medicament for treating relapsing-remitting multiple sclerosis in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention yet also provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the administration pattern of the medicament is three subcutaneous injections of a therapeutically effective dose of glatiramer acetate over a period of seven days with at least one day between every subcutaneous injection.

This invention further provides a use of glatiramer acetate in the preparation of a medicament for increasing the tolerability of GA treatment in a human patient suffering from relapsing-remitting multiple sclerosis or a patient who has experienced a first clinical episode and is determined to be at high risk of developing clinically definite multiple sclerosis wherein the medicament is prepared for an administration pattern of three subcutaneous injections of a therapeutically effective dose of glatiramer acetate over a period of seven days with at least one day between every subcutaneous injection.

This invention provides glatiramer acetate for use in treating relapsing-remitting multiple sclerosis in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

This invention also provides glatiramer acetate for use in increasing the tolerability of GA treatment in a human patient suffering from relapsing-remitting multiple sclerosis or a patient who has experienced a first clinical episode and is determined to be at high risk of developing clinically definite multiple sclerosis by three subcutaneous injections over a period of seven days with at least one day between every subcutaneous injection.

DEFINITIONS

As used herein, immediate post injection reaction (IRPR) refers to a reaction such as, palpitations, feeling hot, flushing, hot flushes, tachycardia, dyspnoea, chest discomfort, chest pain, and non-cardiac chest pain that occurs immediately following injection. Reactions may also include asthenia, back pain, bacterial infection, chills, cyst, face edema, fever, flu syndrome, infection, injection site erythema, injection site hemorrhage, injection site induration, injection site inflammation, injection site mass, injection site pain, injection site pruritus, injection site urticaria, injection site welt, neck pain, pain, migraine, syncope, tachycardia, vasodilatation, anorexia, diarrhea, gastroenteritis, gastrointestinal disorder, nausea, vomiting, ecchymosis, peripheral edema, arthralgia, agitation, anxiety, confusion, foot drop, hypertonia, nervousness, nystagmus, speech disorder, tremor, vertigo, bronchitis, dyspnea, laryngismus, rhinitis, erythema, herpes simplex, pruritus, rash, skin nodule, sweating, urticaria, ear pain, eye disorder, dysmenorrheal, urinary urgency, and vaginal moniliasis.

As used herein, injection site reaction (ISR) refers to a reaction such as erythema, hemorrhage, induration, inflammation, mass, pain, pruritus, urticaria, and welt that Occurs immediately around the site of injection.

As used herein, "tolerability" relates to the level of discomfort associated with GA treatment. Tolerability is associated with the frequency and severity of post injection reactions and injection site reactions. Tolerability influences the period that a patient can follow GA treatment.

As used herein, the term Gd-enhancing lesions, refers to lesions that result from a breakdown of the blood-brain barrier, which appear in contrast studies using gandolinium contrast agents. Gandolinium enhancement provides information as to the age of a lesion, as Gd-enhancing lesions typically occur within a six week period of lesion formation.

As used herein, the term $T_1$-weighted MRI images refers to an MR-image that emphasizes $T_1$ contrast by which lesions may be visualized. Abnormal areas in a $T_1$-weighted MRI image are "hypointense" and appear as dark spots. These spots are generally older lesions.

As used herein, the term $T_2$-weighted MRI image, refers to an MR-image that emphasizes $T_2$ contrast by which lesions may be visualized. $T_2$ lesions represent new inflammatory activity.

As used herein, the term "unit dosage" refers to physically discrete units suited as single administration dose for a subject to be treated, containing a therapeutically effective quantity of active compound in association with the required pharmaceutical carrier, e.g., a syringe.

As used herein, clinically isolated syndrome (CIS) refers to 1) a single clinical attack suggestive of MS and 2) at least one lesion suggestive of MS. As an example, the patient has at least 1 cerebral lesion detectable by an MRI scan and suggestive of multiple sclerosis. As an additional example the lesion is associated with brain tissue inflammation, myelin sheath damage or axonal damage. As another example the lesion is a demyelinating white matter lesion visible on brain MRI. In a further example, the white matter lesions are at least 3 mm in diameter.

The term "single clinical attack" is used synonymously with "first clinical episode", "first clinical attack", and "first clinical event" which, for example, presents as a clinical episode of optic neuritis, blurring of vision, diplopia, involuntary rapid eye movement, blindness, loss of balance, tremors, ataxia, vertigo, clumsiness of a limb, lack of coordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

As used herein, the criteria, as defined by Poser et al. Neurology, March 1983, 13 (3): 227-230, used to determine if a subject meets the condition consistent with clinically definite multiple sclerosis (CDMS) are:
   Two attacks and clinical evidence of two separate lesions or
   Two attacks; clinical evidence of one lesion and paraclinical evidence of another separate lesion.

An attack (also referred to as an exacerbation, flare, or relapse) is defined clinically as the sudden appearance or worsening of a symptom or symptoms of neurological dysfunction, with or without objective confirmation.

Clinical evidence of a lesion is defined as signs of neurological dysfunction demonstrable by neurological examination. An abnormal sign constitutes clinical evidence even if no longer present, but was recorded in the past by a competent examiner.

Paraclinical evidence of a lesion is defined as the demonstration by means of various tests and procedures of the existence of a lesion of the CNS that has not produced clinical signs but that may or may not have caused symptoms in the past. Such evidence may be derived from the hot-bath test, evoked response studies, neuroimaging, and expert neurological assessment. These tests are considered to be extensions of the neurological examination and not laboratory procedures.

As used herein, the term "glatiramoid" refers a complex mixture of the acetate salts of synthetic polypeptides, non-uniform with respect to molecular weight and sequence.

This invention is illustrated in the Examples section which follows. This section is set forth to aid in an understanding of the invention but is not intended to, and should not be construed to, limit in any way the invention as set forth in the claims which follow thereafter.

EXPERIMENTAL DETAILS

Example 1

A multinational, multicenter, randomized, phase III parallel-group study performed in subjects with Relapsing-Remitting Multiple Sclerosis (RRMS) to assess the efficacy, safety and tolerability of Glatiramer Acetate (GA) injection 40 mg/ml administered three times weekly by subcutaneous injection over placebo in a double-blind design.

Methods:

The study is designed to select three days a week for injection. Three injections are administered for every seven days and there must be at least one day between each injection.

Study Duration:

Screening phase: 1 month

Placebo Controlled (PC) Phase: 12 months of 40 mg/ml or matching placebo administered three times weekly by subcutaneous injection.

Open Label (OL) Extension: All subjects will continue treatment with the GA 40 mg/ml administered three times a week, until this dose is commercially available for the treatment of relapsing remitting multiple sclerosis (RRMS) patients or until the development of this dose for MS is stopped by the Sponsor.

Study Population:

Subjects with RRMS

Number of Subjects:

1350 subjects

Study Objective(s):

To assess the efficacy, safety and tolerability of Glatiramer Acetate (GA) injection 40 mg/ml administered three times weekly compared to placebo in a double-blind study design.

Study Design:

Eligible subjects are randomized in a 2:1 ratio (40 mg:placebo) and assigned to one of the following three treatment arms:

1. 40 mg s.c. GA three times weekly (900 subjects)
2. Matching placebo three times weekly (450 subjects)

During the PC phase, subjects are evaluated at study sites for a total of 7 scheduled visits at months: −1 (screening), 0 (baseline), 1, 3, 6, 9, and 12 (End of PC phase).

Subjects successfully completing the study are offered the opportunity to enter into an open label extension in which all subjects will continue treatment with 40 mg/ml GA dose. This is done until the 40 mg/ml GA dose is commercially available for the treatment of relapsing remitting multiple sclerosis (RRMS) patients or until the development of this dose regimen is stopped by the Sponsor.

The termination visit of the PC phase will serve as the baseline visit of the OL phase. This phase will include scheduled visits every 3 months for the first 12 months, then scheduled visits every 6 months and will be completed with a termination visit.

During the study, the following assessments are performed (regardless of the treatment assignment) at the specified time points:

Vital signs are measured at each study visit.

A physical examination is performed at months −1 (screening), 0 (baseline) 6, 12 (end of PC phase) and every 6 months thereafter. In addition, a physical examination will be performed at the termination visit of the OL phase.

The following safety clinical laboratory tests are performed:

Complete blood count (CBC) with differential—at all scheduled visits in the PC phase, and every 12 months thereafter. In addition this test will be performed at the termination visit of the OL phase.

Serum chemistry (including electrolytes, creatinine, urea and liver enzymes) and urinalysis—at all scheduled visits in the PC phase, and every 12 months thereafter. In addition this test will be performed at the termination visit of the OL phase.

Serum β-hCG in women of child-bearing potential is performed at months −1 (screening), 0 (baseline), 12 (end of PC phase), and every 12 months thereafter. In addition this test will be performed at the termination visit of the OL phase.

ECG is performed at months −1 (screening), 0 (baseline), 12 (end of PC phase), and every 12 months thereafter. In addition an ECG will be performed at the termination visit of the OL phase.

Chest X-ray is performed at month −1 (screening) if not performed within 6 months prior to screening visit.

Adverse Events (AEs) are monitored throughout the study.

Concomitant Medications are monitored throughout the study.

Neurological evaluations, including Neurostatus [Functional Systems (FS), Expanded Disability Status Scale (EDSS), Ambulation Index (AI)] are performed at months −1 (screening), 0 (baseline), 3, 6, 9, 12 (end of PC phase) and every 6 months thereafter. In addition, a neurological examination are performed at the termination visit of the OL phase.

The general health status is assessed by the EuroQoL (EQ5D) questionnaire at months 0 (baseline) and 12 (end of PC phase).

Additional quality of life parameters are assessed by the WPAI (Work Productivity and Activities Impairment) Questionnaire at month 0 (baseline), 3, 6, 9 and 12 (end of PC phase).

All subjects undergo MRI scans at months 0 (13-7 days prior to baseline visit), 6 and 12 (end of PC phase). Following the results of the PC phase, the Sponsor may decide to perform an MRI scan at the termination visit of the OL phase.

Relapses are confirmed/monitored throughout the study.

Ancillary Studies:

Blood samples for determination of anti-GA antibodies are collected for all subjects at months 0 (baseline), 1, 3, 6, 9, 12 (end of PC phase), 18 and 24.

Blood samples for evaluation of PBL proliferation in response to GA, as well as other immunological parameters, are collected in a subset of subjects at months 0 (baseline), 1, 3, 6, and 12 (end of PC phase).

Blood samples for Pharmacogenetic (PGx) analysis are collected for all subjects twice during the study, preferably at month 0 (baseline) and month 1.

The allowed treatment for a multiple sclerosis relapse will be intravenous methylprednisolone 1 gr/day for up to 5 consecutive days.

Re-Consent Criteria

In case of a confirmed diagnosis of MS relapse (as defined in the protocol), or in case of an increase in EDSS of 1.5 points or more, sustained for at least 3 months, during the placebo-controlled phase, the following actions are taken:

The subject is reminded of the current available MS medications/treatments and the opportunity to terminate the study.

The subject is requested to re-sign an informed consent form if he/she chooses to continue to participate in the study, in the same treatment assignment.

The study is closely monitored through the study course by the sponsor's personnel as well as by an external independent data monitoring committee (DMC) in order to ensure subjects' welfare.

Inclusion/Exclusion:

Inclusion Criteria:

Subjects must have a confirmed and documented MS diagnosis as defined by the Revised McDonald criteria (Ann Neurol 2005: 58:840-846), with a relapsing-remitting disease course.

Subjects must be ambulatory with an EDSS score of 0-5.5 in both screening and baseline visits.

Subjects must be in a relapse-free, stable neurological condition and free of corticosteroid treatment [intravenous (IV), intramuscular (IM) and/or per os (PO)] or ACTH 30 days prior to screening (month −1) and between screening (month −1) and baseline (month 0) visits.

Subjects must have had experienced one of the following:
  At least one documented relapse in the 12 months prior to screening, or
  At least two documented relapses in the 24 months prior to screening, or
  One documented relapse between 12 and 24 months prior to screening with at least one documented $T_1$-Gd enhancing lesion in an MRI performed within 12 months prior to screening.

Subjects must be between 18 and 55 years of age, inclusive.

Women of child-bearing potential must practice an acceptable method of birth control [acceptable methods of birth control in this study include: surgical sterilization, intrauterine devices, oral contraceptive, contraceptive patch, long-acting injectable contraceptive, partner's vasectomy or a double-barrier method (condom or diaphragm with spermicide)].

Subjects must be able to sign and date a written informed consent prior to entering the study.

Subjects must be willing and able to comply with the protocol requirements for the duration of the study.

Exclusion Criteria:
  Subjects with progressive forms of MS.
  Use of experimental or investigational drugs, and/or participation in drug clinical studies within the 6 months prior to screening.
  Use of immunosuppressive (including Mitoxantrone (Novantron®) or cytotoxic agents within 6 months prior to the screening visit.
  Previous use of either natalizumab (Tysabri®) or any other monoclonal antibodies within 2 years prior to screening.
  Use of cladribine within 2 years prior to screening.
  Previous treatment with immunomodulators (including IFNβ 1a and 1b, and IV Immunoglobulin (IVIg) within 2 months prior to screening.
  Previous use of GA or any other glatiramoid.
  Chronic (more than 30 consecutive days) systemic (IV, PO or IM) corticosteroid treatment within 6 months prior to screening visit.
  Previous total body irradiation or total lymphoid irradiation.
  Previous stem-cell treatment, autologous bone marrow transplantation or allogenic bone marrow transplantation.
  Known human immunodeficiency virus (HIV) positive status.
  Pregnancy or breastfeeding.
  Subjects with a clinically significant or unstable medical or surgical condition that would preclude safe and complete study participation, as determined by medical history, physical exams, ECG, abnormal laboratory tests and chest X-ray. Such conditions may include hepatic, renal or metabolic diseases, systemic disease, acute infection, current malignancy or recent history (5 years) of malignancy, major psychiatric disorder, history of drug and/or alcohol, abuse and allergies that could be detrimental according to the investigator's judgment.
  A known history of sensitivity to Gadolinium.
  Inability to successfully undergo MRI scanning.
  A known drug hypersensitivity to mannitol.

Route and Dosage Form:
  Glatiramer Acetate 40 mg in 1 ml for subcutaneous injection in a pre-filled syringe (PFS), administered three times a week.
  Matching placebo injection (mannitol in 1 ml WFI) for subcutaneous injection in a pre-filled syringe (PFS).

Outcome Measures:

Primary Outcome Measure:
  The total number of confirmed relapses during the 12 month PC phase.

Secondary Outcome Measure:
  The number of new $T_2$ lesions at month 12 (end of PC phase) as compared to baseline scan.
  The cumulative number of enhancing lesions on $T_1$-weighted images taken at months 6 and 12 (end of PC phase).
  Brain atrophy as defined by the percent brain volume change from baseline to month 12 (end of PC phase).

Exploratory Endpoints:
  The following assessments are presented in an exploratory manner.
    The time to the first confirmed relapse during the placebo-controlled phase.
    The proportion of relapse-free subjects during the placebo-controlled phase.
    The total number of confirmed relapses during the placebo-controlled phase requiring hospitalization and/or IV steroids.
    The proportion (%) of subjects with confirmed EDSS progression during the placebo-controlled phase (progression of at least 1 EDSS point sustained for at least 3 months).
    Change from baseline to month 12 (end of placebo-controlled phase) in EDSS Score.
    Change from baseline to month 12 (end of placebo-controlled phase) in Ambulation Index.
    The total volume of $T_2$ lesions at month 12 (end of placebo-controlled phase)
    The number of new hypointense lesions on enhanced $T_1$ scans at month 12 (end of placebo-controlled phase) as compared to the baseline scan.
    The total volume of hypointense lesions on enhanced $T_1$ scans at month 12 (end of placebo-controlled phase).
    Brain atrophy as defined by the percentage change from baseline to month 12 (end of placebo-controlled phase) in normalized gray matter volume and in normalized white matter volume.
    The general health status, as assessed by the EuroQoL (EQ5D) questionnaire.
    Assessment of the effect of general health and symptom severity on work, using the work productivity and activities impairment General Health (WPAI-GH) questionnaire.

Safety and Tolerability Outcome Measures:

Safety:
  Adverse events
  Vital signs
  ECG findings
  Clinical laboratory parameters Tolerability:
  Proportion of subjects (%) who prematurely discontinued from the study, reason of discontinuation and the time to withdrawal.
  Proportion of subjects (%) who prematurely discontinued from the study due to AEs and the time to withdrawal.

Statistical Considerations:

The sample size considerations for the study are based on the following assumptions:

An individual subject's number of confirmed relapses during a one year period reflects a Poisson process with an individual rate of $\lambda i$, and this individual subject rates $\lambda i$ are exponentially distributed with mean $1/\theta$, where $\theta$ is the population's annualized relapse rate. This approach models the total number of confirmed relapses as an Over Dispersed Poisson distribution.

The expected annualized relapse rate in an untreated subject population is $\theta=0.35$ relapses per year.

Treatment with 40 mg s.c. GA three times weekly reduces the subject population annualized relapse rate by 30% or more when compared to the placebo group. That is, the expected annualized relapse rate of the GA treated populations is $\theta=0.245$ relapses per year or less.

In addition, the following are also incorporated in the sample size calculation:

15% of the subjects drop out during the treatment duration. This drop out rate is taken into account in the calculations, as on the average, a subject who drops out of the study contributes 6 months of exposure to the treatment Hochberg's step-up modification to Bonferroni's method is used to maintain the experiment-wise type-I error when comparing multiple treatment arms to placebo, and the p-values for the IAs are calculated using the O'brien-Fleming alpha spending functions.

A simulation study accounting for the above underlying assumptions used the Quasi-Likelihood (over-dispersed) Poisson Regression (SAS® PROC GENMOD), revealed that a total of 1350 subjects (900 subjects in the 40 mg GA arm, and 450 subjects to the placebo arm) provide approximately 90% power to detect a significant difference in the total number of confirmed relapses as described above.

The analysis of the total numbers of confirmed relapses during the study period is based on baseline adjusted Quasi-Likelihood (over-dispersed) Poisson Regression.

The analysis of the number of new $T_2$ lesions at month 12 and of the cumulative number of enhancing lesions on $T_1$-weighted images taken at months 6 and 12 is based on baseline-adjusted Negative Binomial Regression.

The analysis of Brain Atrophy will be based on Analysis of Covariance (ANCOVA).

Results

Primary Outcome Measure:

Treatment with 40 mg s.c. GA three times weekly reduces the subject population annualized relapse rate by 30% or more when compared to the placebo group. Treatment with 40 mg s.c. GA three times weekly is at least as effective as 20 mg s.c. GA daily administration at reducing the subject population annualized relapse rate.

Secondary Outcome Measures:

Treatment with 40 mg s.c. GA three times weekly significantly reduces the number of new $T_2$ lesions at month 12. Treatment with 40 mg s.c. GA three times weekly is at least as effective as 20 mg s.c. GA daily administration at reducing the number of new $T_2$ lesions at month 12.

Treatment with 40 mg s.c. GA three times weekly significantly reduces the cumulative number of enhancing lesions on $T_1$-weighted images taken at months 6 and 12. Treatment with 40 mg s.c. GA three times weekly is at least as effective as 20 mg s.c. GA daily administration at reducing the cumulative number of enhancing lesions on $T_1$-weighted images taken at months 6 and 12.

Treatment with 40 mg s.c. GA three times weekly significantly reduces brain atrophy as defined by the percent brain volume change from baseline to month 12. Treatment with 40 mg s.c. GA three times weekly is at least as effective as 20 mg s.c. GA daily administration at reducing brain atrophy as defined by the percent brain volume change from baseline to month 12.

Exploratory Endpoints:

Treatment with 40 mg s.c. GA three times weekly significantly increases the time to the first confirmed relapse during the placebo-controlled phase. Treatment with 40 mg s.c. GA three times weekly is at least as effective as 20 mg s.c. GA daily administration at increasing the time to the first confirmed relapse during the placebo-controlled phase.

Treatment with 40 mg s.c. GA three times weekly significantly increases the proportion of relapse-free subjects during the placebo-controlled phase. Treatment with 40 mg s.c. GA three times weekly is at least as effective as 20 mg s.c. GA daily administration at increasing the proportion of relapse-free subjects during the placebo-controlled phase.

Treatment with 40 mg s.c. GA three times weekly significantly increases the proportion of relapse-free subjects during the placebo-controlled phase. Treatment with 40 mg s.c. GA three times weekly is at least as effective as 20 mg s.c. GA daily administration at increasing the proportion of relapse-free subjects during the placebo-controlled phase.

Treatment with 40 mg s.c. GA three times weekly significantly reduces the total number of confirmed relapses during the placebo-controlled phase requiring hospitalization and/or IV steroids. Treatment with 40 mg s.c. GA three times weekly is at least as effective as 20 mg s.c. GA daily administration at reducing the total number of confirmed relapses during the placebo-controlled phase requiring hospitalization and/or IV steroids.

Treatment with 40 mg s.c. GA three times weekly significantly reduces the progression of MRI-monitored disease activity in the patient. Treatment with 40 mg s.c. GA three times weekly is at least as effective as 20 mg s.c. GA daily administration at reducing the progression of MRI-monitored disease activity in the patient.

Treatment with 40 mg s.c. GA three times weekly significantly reduces the total volume of $T_2$ lesions at month 12. Treatment with 40 mg s.c. GA three times weekly is at least as effective as 20 mg s.c. GA daily administration at reducing total volume of $T_2$ lesions at month 12.

Treatment with 40 mg s.c. GA three times weekly significantly reduces the number of new hypointense lesions on enhanced $T_1$ scans at month 12 as compared to the baseline scan. Treatment with 40 mg s.c. GA three times weekly is at least as effective as 20 mg s.c. GA daily administration at reducing the number of new hypointense lesions on enhanced $T_1$ scans at month 12 as compared to the baseline scan.

Treatment with 40 mg s.c. GA three times weekly significantly reduces the total volume of hypointense lesions on enhanced $T_1$ scans at month 12. Treatment with 40 mg s.c. GA three times weekly is at least as effective as 20 mg s.c. GA daily administration at reducing the total volume of hypointense lesions on enhanced $T_1$ scans at month 12.

Treatment with 40 mg s.c. GA three times weekly significantly reduces brain atrophy as defined by the percentage change from baseline to month 12 in normalized gray matter volume and in normalized white matter volume. Treatment with 40 mg s.c. GA three times weekly is at least as effective as 20 mg s.c. GA daily administration at reducing brain atrophy as defined by the percentage change from baseline to month 12 in normalized gray matter volume and in normalized white matter volume.

Treatment with 40 mg s.c. GA three times weekly significantly reduces the level of disability as measured by EDSS Score. Treatment with 40 mg s.c. GA three times weekly is at least as effective as 20 mg s.c. GA daily administration at reducing the level of disability as measured by EDSS Score.

Treatment with 40 mg s.c. GA three times weekly significantly reduces the proportion (%) of subjects with confirmed EDSS progression during the placebo-controlled phase (progression of at least 1 EDSS point sustained for at least 3 months). Treatment with 40 mg s.c. GA three times weekly is at least as effective as 20 mg s.c. GA daily administration at reducing proportion (%) of subjects with confirmed EDSS progression during the placebo-controlled phase, (progression of at least 1 EDSS point sustained for at least 3 months).

Treatment with 40 mg s.c. GA three times weekly significantly reduces the change from baseline to month (end of placebo-controlled phase) in EDSS Score. Treatment with 40 mg s.c. GA three times weekly is at least as effective as 20 mg s.c. GA daily administration at reducing the change from baseline to month 12 (end of placebo-controlled phase) in EDSS Score.

Treatment with 40 mg s.c. GA three times weekly significantly reduces the change from baseline to month 12 (end of placebo-controlled phase) in Ambulation Index. Treatment with 40 mg s.c. GA three times weekly is at least as effective as 20 mg s.c. GA daily administration at reducing the change from baseline to month 12 (end of placebo-controlled phase) in Ambulation Index.

Treatment with 40 mg s.c. GA three times weekly significantly reduces the level of disability as measured by EuroQoL (EQ5D) questionnaire. Treatment with 40 mg s.c. GA three times weekly is at least as effective as 20 mg s.c. GA daily administration at reducing the level of disability as measured by EuroQoL (EQ5D) questionnaire.

Treatment with 40 mg s.c. GA three times weekly significantly reduces the level of disability as measured by the work productivity and activities impairment-General Health (WPAI-GH) questionnaire. Treatment with 40 mg s.c. GA three times weekly is at least as effective as 20 mg s.c. GA daily administration at reducing the level of disability as measured by the work productivity and activities impairment-General Health (WPAI-GH) questionnaire.

Discussion

A significant drawback to GA therapy is the requirement of daily injections, which can be inconvenient. Moreover, in all clinical trials, injection-site reactions were seen to be the most frequent adverse reactions and were reported by the majority of patients receiving GA. In controlled studies, the proportion of patients reporting these reactions, at least once, was higher following treatment with GA (70%) than placebo injections (37%). The most commonly reported injection-site reactions, which were more frequently reported in GA vs. placebo-treated patients, were erythema, pain, mass, puritus, edema, inflammation and hypersensitivity.

However, several obstacles and limitations with potential approaches for addressing the drawbacks exist to current GA therapy. Subcutaneous drug delivery is limited, firstly, by the acceptable injection volume. Typically no more than 1 to 2 ml of solution is permitted (Kansara V, Mitre A, Wu Y, Subcutaneous Delivery. Drug Deliv Technol, June 2009; 9(6):38-42). Secondly, the potential exists for drug degradation at the site of injection resulting in reduced bioavailability. Thirdly, based on the physiochemical properties of the drug, potent compounds may become locally trapped in the interstitial space which can lead to further localized irritation, precipitation of the drug and concentration-dependent adverse effects (Kansara V, Mitra A, Wu Y, Subcutaneous Delivery. Drug Deliv Technol, June 2009; 9(6):38-42). Finally, due to the complex pharmacokinetic behavior of a drug, variation in the frequency of administration is unpredictable and requires empirical testing. For example, although controlled clinical trials have demonstrated the efficacy of IFNβ-1b in the treatment of MS, patient compliance, efficacy and tolerability are affected by the dosage regimen used. Merely increasing the dose of IENβ-1b is insufficient to increase efficacy, the frequency of administration must also be increased (Luca Durelli, J Neurol (2003) 250 [Suppl 4]).

Accordingly, the subject application discloses an effective low frequency dosage regimen of GA administration to patients suffering from a relapsing form of multiple sclerosis, including patients who have experienced a first clinical episode and have MRI features consistent with multiple sclerosis. Based on the performance of the dosage regimen in these studies, the administration of three s.c. injections over a period of seven days with at least one day between every injection is also expected to work in the treatment of patients who have experienced a clinically isolated syndrome (CIS). This is based on the fact that the 20 mg daily s.c. injection has been shown to work in PCT International Application No. PCT/US2008/013146 (see International Publication No. WO 2009/070298 and also U.S. Patent Application Publication No. US 2009-0149541 A1).

What is claimed is:

1. A method of treating a human patient suffering from a relapsing form of multiple sclerosis, while inducing reduced severity of injection site reactions in the human patient relative to administration of 20 mg of glatiramer acetate s.c. daily, the method consisting of one subcutaneous injection of 1 ml of a pharmaceutical composition comprising 40 mg of glatiramer acetate on only each of three days during each week of treatment with at least one day without a subcutaneous injection of the pharmaceutical composition between each day on which there is a subcutaneous injection, wherein the pharmaceutical composition is in a prefilled syringe, and wherein the pharmaceutical composition further comprises mannitol and has a pH in the range 5.5 to 7.0,
so as to thereby treat the human patient with reduced severity of injection site reactions relative to administration of 20 mg of glatiramer acetate s.c. daily.

2. The method of claim 1, which induces reduced frequency and severity of immediate post injection reactions and injection site reactions in the human patient relative to administration of 20 mg of glatiramer acetate s.c. daily.

3. The method of claim 1, wherein the human patient has not received glatiramer acetate therapy prior to initiation of the treatment.

4. The method of claim 2, wherein the human patient has not received glatiramer acetate therapy prior to initiation of the treatment.

5. A method for reducing the frequency of relapses by 30% or more as compared to placebo in a human population, for reducing brain atrophy, for reducing the cumulative number of enhancing lesions on T1-weighted images, or for reducing the level of disability as measured by EDSS Score of a human patient suffering from a relapsing form of multiple sclerosis, while inducing reduced severity of injection site reactions in the human patient relative to administration of 20 mg of glatiramer acetate s.c. daily, which method consists of one subcutaneous injection of 1 ml of a pharmaceutical composition comprising 40 mg of glatiramer acetate on only each of three days during each week of treatment with at least one day without a subcutaneous injection of the pharmaceutical composition between each day on which there is a subcutaneous injection, wherein the pharmaceutical composition is in a prefilled syringe, and wherein the pharmaceutical composition further comprises mannitol and has a pH in the range 5.5 to 7.0, so as to thereby reduce the frequency of relapses by 30% or more as compared to placebo in a human population, reduce brain atrophy, reduce the cumulative number of enhancing lesions on T1-weighted images, or reduce the level of disability as measured by EDSS Score of the human patient with reduced severity of injection site reactions relative to administration of 20 mg of glatiramer acetate s.c. daily.

6. The method of claim 5, which reduces brain atrophy and for reducing the frequency of relapses by 30% or more as compared to placebo in a human population.

7. The method of claim 5, which reduces the cumulative number of enhancing lesions on T1-weighted images.

8. The method of claim 5, which reduces the level of disability of the human patient as measured by EDSS Score.

9. The method of claim 5, which induces reduced frequency and severity of immediate post injection reactions and injection site reactions in the human patient relative to administration of 20 mg of glatiramer acetate s.c. daily.

10. The method of claim 5, wherein the human patient has not received glatiramer acetate therapy prior to initiation of the treatment.

11. The method of claim 9, wherein the human patient has not received glatiramer acetate therapy prior to initiation of the treatment.

12. A method for improving the tolerability of glatiramer acetate treatment of a human patient suffering from a relapsing form of multiple sclerosis which is as effective as administration of 20 mg of glatiramer acetate s.c. daily, which method consists of one subcutaneous injection of 1 ml of a pharmaceutical composition comprising 40 mg of glatiramer acetate on only each of three days during each week of treatment with at least one day without a subcutaneous injection of the pharmaceutical composition between each day on which there is a subcutaneous injection, wherein the pharmaceutical composition is in a prefilled syringe, and wherein the pharmaceutical composition further comprises mannitol and has a pH in the range 5.5 to 7.0, so as to thereby treat the human patient as effectively as by administration of 20 mg of glatiramer acetate s.c. daily, and with reduced severity of injection site reactions relative to administration of 20 mg of glatiramer acetate s.c. daily.

13. The method of claim 12, which treats the human patient with reduced frequency and severity of immediate post injection reactions and injection site reactions relative to administration of 20 mg of glatiramer acetate s.c. daily.

14. The method of claim 12, wherein the human patient has not received glatiramer acetate therapy prior to initiation of the treatment.

15. The method of claim 14, wherein the human patient has not received glatiramer acetate therapy prior to initiation of the treatment.

16. A method for improving the tolerability of glatiramer acetate therapy reducing the frequency of relapses, reducing brain atrophy, reducing the cumulative number of enhancing lesions on T1-weighted images, or reducing the level of disability as measured by EDSS Score, of a human patient suffering from a relapsing form of multiple sclerosis as effectively as administration of 20 mg of glatiramer acetate s.c. daily, which method consists of one subcutaneous injection of 1 ml of a pharmaceutical composition comprising 40 mg of glatiramer acetate on only each of three days during each week of treatment with at least one day without a subcutaneous injection of the pharmaceutical composition between each day on which there is a subcutaneous injection, wherein the pharmaceutical composition is in a prefilled syringe, and wherein the pharmaceutical composition further comprises mannitol and has a pH in the range 5.5 to 7.0, so as to thereby reduce the frequency of relapses, reduce brain atrophy, reduce the cumulative number of enhancing lesions on T1-weighted images, or reduce the level of disability as measured by EDSS Score, of the human patient as effectively as by administration of 20 mg of glatiramer acetate s.c. daily, and with reduced severity of injection site reactions relative to administration of 20 mg of glatiramer acetate s.c. daily.

17. The method of claim 16, which reduces the frequency of relapses as effectively as administration of 20 mg of glatiramer acetate s.c. daily.

18. The method of claim 17, which reduces brain atrophy as effectively as administration of 20 mg of glatiramer acetate s.c. daily.

19. The method of claim 18, which reduces the cumulative number of enhancing lesions on T1-weighted images as effectively as administration of 20 mg of glatiramer acetate s.c. daily.

20. The method of claim 19, which reduces the level of disability as measured by EDSS Score as effectively as administration of 20 mg of glatiramer acetate s.c. daily.

21. The method of claim 17, which treats the human patient with reduced frequency and severity of immediate post injection reactions and injection site reactions relative to administration of 20 mg of glatiramer acetate s.c. daily.

22. The method of claim 18, which treats the human patient with reduced frequency and severity of immediate post injection reactions and injection site reactions relative to administration of 20 mg of glatiramer acetate s.c. daily.

23. The method of claim 19, which treats the human patient with reduced frequency and severity of immediate post injection reactions and injection site reactions relative to administration of 20 mg of glatiramer acetate s.c. daily.

24. The method of claim 20, which treats the human patient with reduced frequency and severity of immediate post injection reactions and injection site reactions relative to administration of 20 mg of glatiramer acetate s.c. daily.

25. The method of claim 17, wherein the human patient has not received glatiramer acetate therapy prior to initiation of the treatment.

26. The method of claim 18, wherein the human patient has not received glatiramer acetate therapy prior to initiation of the treatment.

27. The method of claim 19, wherein the human patient has not received glatiramer acetate therapy prior to initiation of the treatment.

28. The method of claim 21, wherein the human patient has not received glatiramer acetate therapy prior to initiation of the treatment.

29. The method of claim 22, wherein the human patient has not received glatiramer acetate therapy prior to initiation of the treatment.

30. The method of claim 23, wherein the human patient has not received glatiramer acetate therapy prior to initiation of the treatment.

* * * * *